US007115382B1

(12) United States Patent
Overgaard et al.

(10) Patent No.: US 7,115,382 B1
(45) Date of Patent: Oct. 3, 2006

(54) METHOD FOR DETECTING IGFBP-4 PROTEASE WITHOUT DETECTING IGFBP-4 PROTEASE/PROMBP COMPLEX

(75) Inventors: Michael Toft Overgaard, Aarhus C (DK); Claus Oxvig, Viby J (DK); Cheryl A. Conover, Rochester, MN (US)

(73) Assignees: Mayo Foundation for Medical Education and Research, Rochester, MN (US); Como Holdings APS, (DK)

( * ) Notice: Subject to any disclaimer, the term of this patent is extended or adjusted under 35 U.S.C. 154(b) by 0 days.

(21) Appl. No.: 09/936,602

(22) PCT Filed: Mar. 15, 2000

(86) PCT No.: PCT/US00/06728

§ 371 (c)(1),
(2), (4) Date: Feb. 8, 2002

(87) PCT Pub. No.: WO00/54806

PCT Pub. Date: Sep. 21, 2000

Related U.S. Application Data

(60) Provisional application No. 60/124,541, filed on Mar. 15, 1999.

(51) Int. Cl.
*G01N 33/573* (2006.01)
*C07K 16/40* (2006.01)

(52) U.S. Cl. ................. 435/7.4; 530/388.26; 530/389.1
(58) Field of Classification Search ................. 435/226; 530/389.1
See application file for complete search history.

(56) References Cited

U.S. PATENT DOCUMENTS 5,876,433 A 3/1999 Lunn
6,172,198 B1 1/2001 Sinosich

FOREIGN PATENT DOCUMENTS

WO WO 94/21686 9/1994
WO WO 99/32620 7/1999
WO WO 00/54806 9/2000

OTHER PUBLICATIONS de Boer et al, Atherosclerosis, Inflammation, and infection. J Pathol. Feb. 2000;190(3):237-43. Review.*
Jacot et al, Effect of glucose on insulin-like growth factor binding protein-4 proteolysis. Endocrinology. Jan. 1998;139(1):44-50.*
Kirpichnikov et al Diabetes mellitus and diabetes-associated vascular disease. Trends Endocrinol Metab. Jul. 2001;12(5):225-30. Review.*
Oxvig et al Circulating human pregnancy-associated plasma protein-A is disulfide-bridged to the proform of eosinophil major basic protein. J Biol Chem. Jun. 15, 1993;268(17):12243-6.*

Epstein et al Synthetic phosphopeptide immunogens yield activation-specific antibodies to the c-erbB-2 receptor. Proc Natl Acad Sci U S A. Nov. 1, 1992:89(21);10435-9.*
Harlow and Lane Immunoaffinity pruification of antibodies on an antigen column In: Antibodies, a laboratory manual. Cold Spring Harbor Laboratory Press, Cold Spring Harbor, N.Y. pp 313.*
Mazerbourg et al. The insulin-like growth factor system: a key determinant role in the growth and selection of ovarian follicles? a comparative species study. Reprod Domest Anim. Aug. 2003;38(4):247-58 Review.*
Govoni et al. The multi-functional role of insulin-like growth factor binding proteins in bone. Pediatr Nephrol. Mar. 2005;20(3):261-8.*
Mohan et al. Insulin-like growth factor system components and the coupling of bone formation to resorption. Horm Res. 1996;45 Suppl 1;59-62.*
Lawrence et al., "Characterization and partial purification of the insulin-like growth factor (GF)-dependent IGF binding protein-4-specific protease from human fibroblast conditioned media," Growth Hormone & IGF Research, 1999, 9:25-34.
GenBank Accession No. J02642.
GenBank Accession No. J04038.
GenBank Accession No. M10277.
GenBank Accession No. M34462.
GenBank Accession No. X00351.
GenBank Accession No. X14088.
GenBank Accession No. X68280.
Ausubel et al. (eds.), *Short Protocols In Molecular Biology*, 2nd Edition, 1992, Chapter 11, Greene Publishing Associates and John Wiley & Sons, New York, pp. 11-1—11-54.
Bersinger and Klopper, "The pattern of serum levels of pregnancy-associated plasma protein A (PAPP-A) during the ovulatory mentrual cycle," *Br. J. Obstet. Gynaecol.*, 1984, 91;1245-1248.
Bischof et al., "Is pregnancy-associated plasma protein A a tumor marker?" *Am. J. Obstet. Gynecol.*, 1982, 143:379.
Bono et al., "Localization of Pregnancy-Associated Plasma Protein-A and Colocalization of Prenancy-Associated Plasma Protein-A Messenger Ribonucleic Acid and Eosinophil Granule Major Basic Protein Messenger Ribonucleic Acid in Placenta," *Lab. Invest.*, 1994, 71(4);560-566.
Cataldo et al., "Regulation of Insulin-Like Growth Factor Binding Protein Production by Human Luteinizing Granulosa Cells Cultured in Defined Medium," *J. Clin. Endocrinol. Metab.*, 1993, 76:207-215.
Cataldo et al., "Interferon-γ and Activin A Promote Insulin-Like Growth Factor-Binding Protein-2 and -4 Accumulation by Human Luteinizing Granulosa Cells, and Interferon-γ Promotes Their Apoptosis," *J. Clin. Endocrinol. Metab.*, 1998, 83:179-186.
Chandrasekher et al., "Estrogen- But Not Androgen-Dominant Human Ovarian Follicular Fluid Contains an Insulin-Like Growth Factor Binging Protein-4 Protease," *J. Clin. Endocrinol. Metab.*, 1995, 80(9):2734-2739.

(Continued)

*Primary Examiner*—Sheridan L. Swope
(74) *Attorney, Agent, or Firm*—Fish & Richardson P.C., P.A.

(57) ABSTRACT

Methods for screening for altered focal proliferation states in non-pregnant patients, which include detecting levels of pregnancy-associated plasma protein-A (PAPP-A) are described. Methods for identifying agents that alter the protease activity of PAPP-A, and pharmaceutical compositions and medical devices that include such agents are also described.

1 Claim, 5 Drawing Sheets

OTHER PUBLICATIONS

Chandrasekher et al., "Role of Insulin-Like Growth Factor Binding Protein-4 (IGFBP-4) and IGFBP-4 Protease in Human Granulosa Cell Function," *Proceedings of the 28th Annual Meeting of the Society for the Study of Reproduction*, 1995, Davis, California, pp. 82, Abstratct # 102.

Conover et al., "Posttranslational Regulation of Insulin-like Growth Factor Binding Protein-4 in Normal and Transformed Human Fibroblasts," *J. Clin. Invest.*, 1993, 91:1129-1137.

Conover et al., "Evidence That The Insulin-Like Growth Factor Binding Protein-4 Protease In Human Ovarian Follicular Fluid Is Pregnancy Associated Plasma Protein-A," *J. Clin. Endocrinol. Metab.*, 1999, 84(12):4742-4745.

Durham et al., "Alterations in Insulin-Like Growth Factor (IGF)-Dependent IGF-Binding Protein-4 Proteolysis in Transformed Osteoblastic Cells," *Endocrinology*, 1995, 136(4):1374-1380.

Haaning et al., "Complete cDNA sequence of the preproform of human pregnancy-associated plasma protein-A—Evidence for expression in the brain and induction by cAMP," *Eur. J. Biochem.*, 1996, 237:159-163.

Huse et al., "Generation of a Large Combinatorial Library of the Immunoglobulin Repertoire in Phage Lambda," *Science*, 1989, 246:1275-1281.

Iwashita et al., "Physiological Role of Insulin-Like-Growth-Factor-Binding Protein-4 in Human Folliculogenesis," *Horm. Res.*, 1996, 46(Suppl. 1):31-36.

Kristensen et al., "Amino Acid Sequence of Human Pregnancy-Associated Plasma Protein-A Derived from Cloned cDNA," *Biochem.*, 1994, 33:1592-1598.

Kuhajda and Eggleston, "Pregnancy-Associated Plasma Protein A," *Am. J. Pathol.*, 1985, 121:342-348.

Lawrence et al., "The insulin-like growth factor (IGF)-dependent IGF binding protein-4 protease secreted by human fibroblasts is pregnancy-associated plasma protein-A," *Proc. Natl. Acad. Sci. USA*, 1999, 96:3149-3153.

Lin et al., "Characterization of four human pregnancy-associated plasma proteins," *Am. J. Obstet. Gynecol.*, 1974, 118(2):223-236.

Overgaard et al., "Messenger Ribonucleic Acid Levels of Pregnancy-Associated Plasma Protein-A and the Proform of Eosinophil Major Basic Protein: Expression in Human Reproductive and Nonreproductive Tissues," *Biology of Reproduction*, 1999, 61:1083-1089.

Oxvig et al., "Isolation and characterization of circulating complex between human pregnancy-associated plasma protein-A and proform of eosinophil major basic protein," *Biochim. Biophys. Acta*, 1994, 1201:415-423.

Qin et al., "Double-monoclonal immunofluorometric assays for pregnancy-associated plasma protein A/proeosinophil major basic protein (PAPP-A/proMBP) complex in first-trimester maternal serum screening for Down syndrome," *Clin. Chem.*, 1997, 43(12):2323-2332.

Qin et al., "Studies on the Role of Human Insulin-like Growth Factor-II (IF-II)-Dependent IGF Binding Protein (hIGFBP)-4 Protease in Human Osteoblasts Using Protease-Resistant IGFBP-4 Analogs," *J. Bone Mineral Res.*, 1999, 14(12):2079-2088.

Schwartz et al., "Restenosis After Balloon Angioplasty—A Practical Proliferative Model in Porcine Coronary Arteries," *Circulation*, 1990, 82:2190-2200.

Seppäläet al., "Pregnancy Proteins in Seminal Plasma, Seminal Vesicles, Preovulatory Follicular Fluid, and Ovary," *Annals of the New York Academy of Sciences*, 1985, 442:212-226.

Sjöberg et al., "Hypertimulated human preovulatory follicular fluid, luteinized cells of unruptured follicles, and corpus luteum contain pregnancy-associated plasma protein A (PAPP-A)," *Fertility and Sterility*, 1984, 41(4):551-557.

Van Dessel et al., "Serum and Follicular Fluid Levels of Insulin-Like Growth Factor I (IGF-I), IGF-II, and IGF-Binding Protein-1 and —3 during the Normal Menstrual Cycle," *J. Clin. Endocrinol. Metab.*, 1996, 81(3):1224-1231.

* cited by examiner

IGFBP-4 Protease: PAPP-A mRNA Expression Vascular Smooth Muscle Cells

METHOD FOR DETECTING IGFBP-4 PROTEASE WITHOUT DETECTING IGFBP-4 PROTEASE/PROMBP COMPLEX

This application is a US §371 filing of PCT/US00/06728, filed Mar. 15, 2000 and published as WO 00/54806 on Sep. 21, 2000, and claims the benefit of provisional application U.S. 60/124,541, filed Mar. 15, 1999, which expired Sep. 21, 2001.

TECHNICAL FIELD

The invention relates to uses of pregnancy-associated plasma protein-A as a marker and therapeutic target for focal growth states in non-pregnant patients.

BACKGROUND

Proteolytic cleavage of the six known insulin-like growth factor binding proteins (IGFBPs) is a powerful means of rapid structure and function modification of these important growth-regulatory proteins. Intact IGFBP-4 is a potent inhibitor of insulin-like growth factor (IGF) action in vitro, and cleavage of IGFBP-4 has been shown to abolish its ability to inhibit IGF stimulatory effects in a variety of systems, suggesting that IGFBP-4 proteolysis acts as a positive regulator of IGF bioavailability.

SUMMARY

The invention is based, in part, on the isolation of an IGF-dependent IGFBP-4-specific protease from human fibroblast-conditioned media (HFCM) and its identification as pregnancy-associated plasma protein-A (PAPP-A), a protein found in high concentrations in the maternal circulation during pregnancy. Identification of PAPP-A as the IGF-dependent IGFBP-4 protease provides methods for screening for altered proliferation states in non-pregnant patients, including growth-promoting and growth-inhibiting states. Identification of PAPP-A as an IGFBP-4 protease also provides a therapeutic target for agents that enhance or inhibit the protease activity of PAPP-A, which in turn regulates the level of bioavailable IGF.

In one aspect, the invention features methods for screening for a growth-promoting or growth-inhibiting state in a non-pregnant patient. The method includes detecting a level of PAPP-A in a biological sample from the non-pregnant patient and comparing the level of PAPP-A in the non-pregnant patient to a standard level of PAPP-A in non-pregnant patients. The biological sample can be selected from the group consisting of blood, urine, pleural fluid, oral washings, tissue biopsies, and follicular fluid. An increase in the level of PAPP-A in the non-pregnant patient indicates the presence of a growth-promoting state, whereas a decrease in the level of PAPP-A indicates the presence of a growth-inhibiting state. For example, the growth-promoting state can be restenosis, atherosclerosis, ovulation, wound healing, fibrosis, and cancer. Growth-inhibiting states can be, for example, osteoporosis or cancer.

The level of PAPP-A can be measured as PAPP-A protease activity, or as an amount of PAPP-A protein or messenger RNA. PAPP-A protein can be detected immunologically, for example, by at least one monoclonal antibody. PAPP-A can be detected in a PAPP-A complex with at least one other protein, for example, pro-major basic protein, as a dimer of PAPP-A, or as a PAPP-A monomer.

The invention also features a monoclonal antibody having specific binding affinity for PAPP-A, wherein PAPP-A is free of pro-major basic protein and methods for making such monoclonal antibodies. The method includes immunizing a host animal with a PAPP-A polypeptide to obtain antibody clones, wherein the PAPP-A polypeptide is free of pro-major basic protein. Monoclonal antibodies having binding affinity for PAPP-A, but not for a PAPP-A/pro-major basic protein complex, then are selected. Methods for detecting PAPP-A in a biological sample also are featured that include contacting the biological sample with an antibody having specific binding affinity for PAPP-A, but not PAPP-A/pro major basic protein complex, to detect PAPP-A in the biological sample.

In another aspect, the invention relates to a pharmaceutical composition that includes a pharmaceutically acceptable carrier and an agent that alters the protease activity of PAPP-A, as well as methods for identifying such agents. The methods for identifying inhibitors of PAPP-A activity include incubating an isolated PAPP-A polypeptide, an activator of protease activity, and a substrate of PAPP-A, such as IGFBP-4, with the agent to determine if proteolysis of the substrate is inhibited. The activator of protease activity can be insulin-like growth factor I or insulin-like growth factor II. The methods for identifying agents that enhance the protease activity of PAPP-A include incubating an isolated PAPP-A polypeptide and a substrate of PAPP-A (e.g., IGFBP-4) with the agent to determine if proteolysis of the substrate is enhanced. PAPP-A can be immobilized. For example, the agent that enhances PAPP-A activity can be a fragment of an insulin-like growth factor.

The invention also relates to a medical device for placement in a patient that includes an agent that alters PAPP-A protease activity. The agent can enhance or inhibit PAPP-A protease activity. The medical device can be impregnated or coated with the agent. The inhibitor of PAPP-A protease activity can be, for example, pro MBP, an antibody or a metalloprotease inhibitor, such as 1,10-phenanthroline. The medical device can be a stent for placement in a lumen of the patient.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. In case of conflict, the present specification, including definitions, will control. In addition, the materials, methods and examples are illustrative only and not intended to be limiting.

Other features and advantages of the invention will be apparent from the following detailed description, and from the claims.

DESCRIPTION OF DRAWINGS

FIG. 1A indicates that IGFBP-4 protease activity in the absence (−) or presence (+) of added IGF-II is inhibited by presence of the indicated titer of polyclonal PAPP-A/pro major basic protein (MBP) antibodies (anti-PAPP-A), but not in the presence of the indicated titer of nonspecific rabbit IgG. FIG. 1B indicates the immunodepletion of IGFBP-4 protease activity from HFCM. HCFM was precleared with a 1:50 titer of non-specific rabbit IgG, followed by immunodepletion with the indicated titer of PAPP-A antibodies, and then assayed for IGFBP-4 protease activity in the absence (−) or presence (+) of added IGF-II. FIG. 1C indicates the IGF-dependent IGFBP-4 protease activity of PAPP-A/proMBP (0.5 μg) purified from pregnancy sera in the absence (−) or presence (+) of 5 nM IGF-II.

FIG. 6A shows anion exchange chromatography on a Mono Q HR 10/10 column. Pregnancy serum (3.2 ml) was diluted with water, loaded onto the column, and eluted with a gradient of increasing salt concentration. The flow rate was 1 ml/min, and fractions of 1 ml were collected. The concentration of PAPP-A antigen was measured in all fractions by ELISA and plotted onto the chromatogram. Note that the PAPP-A axes have logarithmic scales. Recombinant PAPP-A expressed in mammalian cells elute around fraction 24. FIG. 6B is a Western blot of chromatographic fractions separated in 3–8% SDS-PAGE. Pregnancy serum PAPP-A eluting early and late from the anion exchanger was analyzed with a PAPP-A specific monoclonal antibody, 234-2. Fractions around fraction 24 (fractions 22-25) were pooled and PAPP-A antigen was purified by heparin chromatography and loaded onto the gel (lane 1). Material from fraction 43 (late eluting PAPP-A) was loaded directly onto the gel (lane 2). The one band in lane 2 reacted with a proMBP specific MAB. Of the two bands visible in lane 1, only the upper reacted with a proMBP specific mAb, 234-10.

DETAILED DESCRIPTION

Figure 1A:
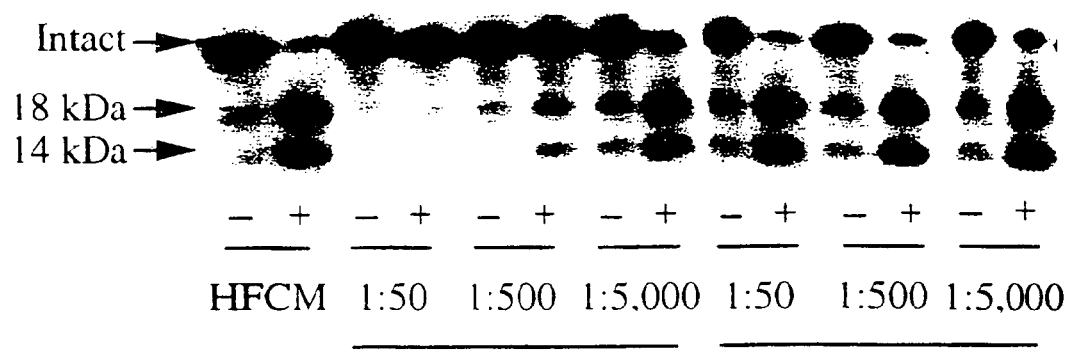
FIGS. 1A–1C are autoradiograms that confirm identity of the IGF-dependent IGFBP-4 protease as PAPP-A.

Insulin-like growth factors (IGFs) are essential polypeptides with potent anabolic and mitogenic actions both in vivo and in vitro. IGF bioactivity is modulated by distinct high-affinity IGF binding proteins (IGFBPs), six of which have been identified to date. IGFBPs can undergo limited proteolysis with consequent modification of IGFBP structure and function, and hence IGF action.

An IGFBP4-specific metalloprotease activity is secreted by normal human fibroblasts in culture. Incubation of IGFBP-4 in human fibroblast-conditioned medium (HFCM) under cell-free conditions results in cleavage of IGFBP-4 (about 24 kDa nonreduced, about 32 kDa reduced) in the midportion of the molecule producing distinct fragments of about 18 and about 14 kDa. The defining feature of this IGFBP-4 proteolytic reaction is its absolute dependence on IGFs for functional activity. Only very low concentrations of IGFs are needed, and, in general, IGF-II is more potent than IGF-I in activating proteolysis. Similar IGF-dependent IGFBP-4 proteolysis has been described in, for example, cultures of normal human osteoblasts, vascular smooth muscle cells, endometrial stromal cells, decidual cells, and granulosa cells, as well as in ovarian follicular fluid. Previously, the responsible enzyme was not known to be PAPP-A, making delineation of a physiological role for IGFBP-4 proteolysis extremely difficult.

As described herein, the IGF-dependent IGFBP-4 protease has been purified from HFCM and identified as PAPP-A. The terms "IGFBP-4 protease" and "PAPP-A" are used interchangeably throughout the text. PAPP-A has been described as a large placental glycoprotein, present in the serum of pregnant women in increasing concentrations throughout pregnancy. PAPP-A in pregnancy serum is disulfide linked to the proform of eosinophil major basic protein (proMBP), forming an approximately 500 kDa 2:2 complex, denoted PAPP-A/proMBP. PAPP-A and proMBP are both produced in the placenta during pregnancy, but mainly in different cell types as shown by in situ hybridization. In this tissue, the vast majority of PAPP-A is synthesized in the syncytiotrophoblast, and all proMBP is synthesized in extracellular trophoblasts.

The cDNA sequence of PAPP-A indicates that the serum form is derived from a pre-proprotein with a putative 22-residue signal peptide, a pro-part of 58 residues, and an 1547-residue circulating mature polypeptide. The sequence shows no global similarity to any known protein, but it contains two sequence motifs common to the metzincins, a superfamily of metalloproteases, three Lin-12/Notch repeats known from the Notch protein superfamily, and five short consensus repeats known from components of the complement system. PAPP-A not complexed with proMBP has not been isolated from pregnancy serum, but, as described herein, can be isolated from conditioned media from human fibroblasts, human osteoblasts, human coronary artery smooth muscle cells, and from mammalian cells transfected with PAPP-A cDNA. It has been reported that the PAPP-A/proMBP complex is absent from maternal serum in pregnancies where the mother is carrying a fetus with Cornelia de Lange syndrome. Recently, PAPP-A and proMBP in conjuction with SP1 have been shown to be effective markers for detecting fetuses affected with Down's syndrome in weeks 7–12 of gestation.

The identification of PAPP-A as the IGF-dependent IGFBP-4 protease has immediate ramifications for placental function and fetal development. In addition, the identification of the IGF-dependent IGFBP-4 protease as PAPP-A, and the availability of pure protein and associated molecular tools now allows determination of the mechanism underlying its IGF dependence and the biological role of localized IGF-dependent IGFBP-4 proteolysis in such diverse systems as wound healing, bone remodeling, cancer, atherosclerosis, and follicular development.

Therefore, identification of PAPP-A as the IGFBP-4 protease provides methods for screening for altered focal proliferation states in nonpregnant patients. "Altered focal proliferation states" refer to both growth-promoting and growth-inhibiting states. As used herein, "growth-promoting" refers to one or more of an increase in cell number, increase in cell size, or an increase in differentiated cell function. Non-limiting examples of growth-promoting states include atherosclerosis, restenosis, fibrosis, wound healing, IGF dependent growth of cancer cells, and ovulation including follicular development. "Growth-inhibiting" refers to a decrease in cellular growth-rate or cell size, and includes osteoporosis and tissues/cells in the vicinity of cancers. Cancer cells can have down-regulated expression of PAPP-A, as cancer cells typically do not depend on IGFs for growth. Decreased expression of PAPP-A may disadvantage surrounding cells, as the surrounding cells depend on IGF. Nonpregnant patients are examined, as the large elevation in PAPP-A levels in pregnancy would obscure smaller changes in the PAPP-A level. Serum PAPP-A levels under normal conditions in healthy male volunteers are low, but detectable (4.32±1.54 mIU/L; n=30). In comparison, PAPP-A rises during pregnancy to approximately 100,000 mIU/L at term.

Detection of PAPP-A Protein

A biological sample from a nonpregnant patient is assessed for the level of PAPP-A, including level of PAPP-A protein, message (mRNA), or activity. Suitable biological samples include, for example, blood, urine, pleural fluid, oral washings, tissue biopsies such as skin, bone, or blood vessel plaque, and follicular fluid. Blood is a particularly useful biological sample.

PAPP-A protein can be detected, for example, immunologically. For example, a sandwich assay can be performed by capturing PAPP-A from a biological assay with an antibody having specific binding affinity for PAPP-A. PAPP-A then can be detected with a labeled antibody having specific binding affinity for PAPP-A. Alternatively, standard immunohistochemical techniques can be used to detect PAPP-A protein, using such antibodies. Antibodies having affinity for PAPP-A/proMBP complexes are available. See, for example, Qin et al., Clin. Chem., 1997, 43(12):2323–2332. Monoclonal antibodies having specific binding affinity for PAPP-A, but not for PAPP-A/proMBP complexes, can be produced through standard methods. In pregnancy plasma and serum about 1% of PAPP-A is not complexed with proMBP protein, but rather exists as a noncomplexed PAPP-A dimer. Measurements of the fraction of uncomplexed PAPP-A using a monoclonal antibody that recognizes the uncomplexed form of PAPP-A only is different from measuring total PAPP-A with either polyclonal or monoclonal antibodies. Measurement of uncomplexed PAPP-A in pregnancy serum potentially has a diagnostic value. Because proMBP functions as a inhibitor of PAPP-A activity, the amount of uncomplexed PAPP-A can also be estimated by measuring the PAPP-A activity of a given sample.

In general, PAPP-A not complexed to proMBP can be produced in various ways, including recombinantly, or can be purified from a biological sample, and used to immunize animals. To produce recombinant PAPP-A, a nucleic acid sequence encoding PAPP-A polypeptide can be ligated into an expression vector and used to transform a bacterial or eukaryotic host cell. In general, nucleic acid constructs include a regulatory sequence operably linked to a PAPP-A nucleic acid sequence. Regulatory sequences do not typically encode a gene product, but instead affect the expression of the nucleic acid sequence. In bacterial systems, a strain of Escherichia coli such as BL-21 can be used. Suitable E. coli vectors include the pGEX series of vectors that produce fusion proteins with glutathione S-transferase (GST). Transformed E. coli are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express PAPP-A can be produced by using expression vectors with the appropriate control elements and a selectable marker. For example, the eukaryotic expression vector pcDNA.3.1+(Invitrogen, San Diego, Calif.) is suitable for expression of PAPP-A in, for example, COS cells or HEK293 cells. Following introduction of the expression vector by electroporation, DEAE dextran, or other suitable method, stable cell lines are selected. In an expression system using pcDNA3.1+ and HEK293 cells, yield of the protein was about 5 µg/ml. The secreted product was a dimer devoid of proMBP. Alternatively, PAPP-A can be transcribed and translated in vitro using wheat germ extract or rabbit reticulocyte lysase.

In eukaryotic host cells, a number of viral-based expression systems can be utilized to express PAPP-A. A nucleic acid encoding PAPP-A can be cloned into, for example, a baculoviral vector and then used to transfect insect cells. Alternatively, the nucleic acid encoding PAPP-A can be introduced into a SV40. retroviral or vaccinia based viral vector and used to infect host cells.

As described herein, recombinant PAPP-A (rPAPP-A) is immunoreactive against all available monoclonal antibodies in ELISA and in Western blotting. Recombinant PAPP-A is secreted as a homodimer of about 400 kDa; and after reduction yields monomers slightly smaller than the 200 kDa subunit from pregnancy serum PAPP-A because of a lower degree of glycosylation. rPAPP-A is active and cleaves IGFBP-4 in an IGF dependent manner. Recombinant PAPP-A is about 100-fold more active than PAPP-A in pregnancy serum.

PAPP-A can be purified, as described herein. For example, PAPP-A can be purified from HFCM by passing over iminodiacetic acid immobilized to Sepharose 6B loaded with $Zn^{+2}$. After elution of bound proteins with a stepwise decreasing pH gradient, the pH 5.0 fraction can be purified further by passing over a wheat gem agglutinin column. Bound proteins can be eluted with a Tris-salt solution, then by N-acetlglucosamine. Alternatively, a heparin sepharose column can be used and PAPP-A is eluted with an increase in salt concentration to 1000 mM. Fractions containing PAPP-A, as measured with PAPP-A specific antibodies or with a specific protease activity assay, can be pooled, concentrated, then assessed by SDS polyacrylamide gel electrophoresis. In reducing SDS/PAGE, the molecular mass of PAPP-A monomer is approximately 200 kDa.

Various host animals can be immunized by injection of PAPP-A. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a PAPP-A polypeptide and standard hybridoma technology. In particular, monoclonal antibodies can be obtained by any technique that provides for the production of antibody molecules by continuous cell lines in culture such as described by Kohler, G. et al., Nature, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77–96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

Antibody fragments that have specific binding affinity for PAPP-A polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of PAPP-A by standard immunoassay methods including ELISA techniques, radioimmunoassays and Western blotting. See. *Short Protocols in Molecular Biology*, Chapter 11, Green Publishing Associates and John Wiley & Sons, Edited by Ausubel, F. M et al., 1992. Antibodies having affinity for PAPP-A are identified in a positive selection. Antibodies identified in such a selection can be negatively selected against PAPP-A/proMBP, to identify antibodies having specific binding affinity for epitopes of PAPP-A that are not accessible in the specific complex of PAPP-A and proMBP.

Detection of PAPP-A Message

PAPP-A message can be detected by a polymerase chain reaction (PCR) assay. In general, PCR refers to amplification of a target nucleic acid, using sequence information from the ends of the region of interest or beyond to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described for example in *PCR Primer: A Laboratory Manual*, Ed. by Dieffenbach. C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R., *Genetic Engineering News*, 12(9):1 (1992); Guatelli et al., *Proc. Natl. Acad. Sci. USA*, 87:1874–1878 (1990); and Weiss, R., *Science*, 254:1292 (1991).

For example, the levels of PAPP-A mRNA can be detected using a sensitive, semi quantitative reverse transcription-polymerase chain reaction (RT-PCR) assay. The method is based on coamplification of the PAPP-A cDNA and a deletion variant thereof, which is used as an internal standard (IS). The amount of PAPP-A is normalized against the total amount of mRNA in the sample, determined as the amount of β-actin mRNA. RT-PCR has been shown to be 1,000–10,000 fold more sensitive than traditional RNA blotting techniques, and was able to detect and quantitate both PAPP-A and proMBP mRNA in all the tissues tested. In a number of these tissues, such as colon, prostate, uterus (endometrium and myometrium), neither PAPP-A nor proMBP mRNA were detectable when screening the commercial RNA dot blot with PAPP-A or proMBP specific probes.

Products from competitive PCR can be quantified by ion exchange chromatography on an HPLC system, an accurate method that involves a minimum of post-PCR handling. For example, samples with about equal amounts of cDNA and IS PCR-products, as judged by gel-electrophoresis, can be separated on a Hewlett-Packard 1084 HPLC instrument equipped with a Waters Gen-Pak4,41J FAX nonporous ion-exchange column using a linear salt gradient. A dilution value, DIeq, is the dilution which would result in approximately equimolar amounts of cDNA and IS PCR products, and can be calculated from equation 1:

$$DI_{eq(x)} = D \times \frac{CP}{IP}, \quad (1)$$

CP is the amount of cDNA PCR product, determined as the total $A_{260}$ absorption; IP is the amount of IS PCR product, determined as the total $A_{260}$ absorption corrected for the difference in size from the cDNA product; D is the actual dilution of the cDNA preparation; and DIeq(x) is the dilution that would result in equal molar amounts of IS and cDNA PCR product (x is either PAPP-A, proMBP, β-actin, or GADPH).

The specific abundance of PAPP-A or proMBP mRNA, Ax, can be determined (equation 2):

$$A_x = \frac{DI_{eq(x)}}{DI_{eq(\beta-actin)}}, \quad (2)$$

(2)

where:

A(x) is the specific abundance of individual mRNA species.

Thus, the specific abundance is a measure of the mRNA level of the gene of interest, normalized against a measure of the total mRNA in the sample. Given a constant amount of β-actin mRNA molecules per cell, which is a reasonable assumption, the specific abundance, A, is independent of the amount of tissue used. As described herein PAPP-A and proMBP were significantly more abundant in term placenta, than in other tissues analyzed. All tissues analyzed, including endometrium, myometrium, colon, and kidney, contained both PAPP-A and proMBP mRNA.

Variations of this method include real-time quantitative PCR using the ABI PRISM 7700 Sequence Detection System and Taqman fluorogenic probes. An internal reference is used, such as amplification of the 28S rRNA with limiting primer concentration. This method allows quantitation down to approximately 500 copies of the target sequence.

Alternatively, testing different tissues for the presence of specific mRNAs can be done routinely by RNA blotting techniques such as Northern or dot blotting. As described herein, PAPP-A and proMBP mRNAs were detected in a range of tissues by screening either a commercial RNA dot blot or Northern blot containing normalized amounts of RNA from different human tissues. PAPP-A was detected in placenta, and in non-placental tissues such as kidney, heart, adrenal cortex, adrenal medulla, testes, small intestine, and stomach. PAPP-A was detected in low levels in non-placental tissues.

As described herein, the specific abundance of PAPP-A and proMBP mRNA differs greatly between tissues; term placenta has more than 200 fold higher levels than any non-placental tissue tested, verifying that the main site of both PAPP-A and proMBP synthesis during pregnancy is the placenta. Low mRNA levels of non-placental tissues are reflected in the very low serum concentrations of PAPP-A and proMBP antigen in non-pregnant individuals. Both PAPP-A and proMBP are among the most highly expressed genes in placenta, representing 1% (PAPP-A) and 5% (proMBP) of the total number of clones in two placental cDNA libraries (UniGene at http://www.ncbi.nlm.nih.gov/UniGene/Hs.Home.html library 398 and 399, respectively). In these libraries, PAPP-A and proMBP clones were among the five most abundant. Therefore, the mRNA specific abundances calculated here for a number of tissues are low compared to the levels in placenta. In placenta, both PAPP-A and proMBP mRNA are readily detected by in situ hybridization.

The finding that PAPP-A mRNA is synthesized in all the examined tissues, reproductive, as well as non-reproductive, indicates that PAPP-A functions outside pregnancy. Because most tissues analyzed transcribe only one of the two mRNA species, proMBP may be required either for function of PAPP-A or for regulation of PAPP-A activity. Specifically, proMBP may be an inhibitor of PAPP-A proteolytic activity. Measurable PAPP-A activity in pregnancy serum appears to stem from a small fraction of PAPP-A that is present as an uninhibited PAPP-A dimer. In the majority of tissues, the mRNA abundance relative to term placenta is higher for PAPP-A than proMBP. Still, however, the molar concentration of PAPP-A in the tissue may not necessarily exceed that of proMBP. All mRNA levels are expressed relative to the level in term placenta, where the proMBP mRNA abundance is higher that that of PAPP-A. Interestingly, in the tissues where proMBP or MBP are known to be present in excess of PAPP-A, i.e., bone marrow cells (eosinophil leukocytes) and placenta, the specific abundance of proMBP mRNA is higher than that of PAPP-A relative to term placenta.

Earlier reports on localization of PAPP-A in tissues have resulted in contradicting results, and the question of non-placental PAPP-A synthesis has been a subject of controversy. All previous investigations have been based on polyclonal antisera, and a number of reports have appeared describing the polyspecificity and heterogeneity of different preparations of these antisera. Antisera preparations have been purified to minimize the polyspecificity, but polyclonal antisera raised against PAPP-A, now known to be PAPP-A/proMBP, invariably will recognize the proMBP part of the PAPP-A/proMBP complex, mature eosinophil MBP, as well as SP1 and haptoglobin.

In situ hybridization also can be used to detect PAPP-A message. This technique has the advantage that it locates the cells that synthesize the mRNA, but also is less sensitive than RT-PCR. As described herein, mRNA levels in several of the tissues are relatively low, indicating that the synthesis of PAPP-A and proMBP mRNA probably is limited to a few specific cells in the tissue.

Detection of PAPP-A Activity

PAPP-A activity can be detected by examining IGFBP-4 proteolytic activity in a biological sample. For example, a detectable labeled substrate can be incubated in the presence of the biological sample under suitable conditions, and proteolytic products then are detected. The substrate can be, for example, IGFBP-4 or a fragment thereof. In general, the reaction can be carried out at 37° C. in a buffer such as 2 mM $CaCl_2$/50 mM Tris (pH 7.5), including IGF-II or fragments thereof, or any other protease activator. Typically, the substrate is labeled radioactively with isotopes such as $^{251}$ or $^{32}$P, or non-radioactively labeled with biotin, digoxygenin, or a fluorophore. Proteolysis of IGFBP-4 is detected, for example, by examining proteolysis products, such as the 18 and 14 KDa reaction products of IGFBP-4. Radioactive proteins can be separated by reducing 15% SDS/PAGE and visualized by autoradiography. Proteolytic cleavage products also can be detected by immunoblotting.

PAPP-A activity also can be detected after capturing PAPP-A with polyclonal or monoclonal antibodies immobilized, for example, in a well of a microtiter plate. After washing away unbound protein of the biological sample, the activity of PAPP-A can be measured with a low molecular weight synthetic substrate that liberates a colored product that can be detected spectrophotometrically. IGF-II or other activator of PAPP-A can be added with the substrate.

Additionally, PAPP-A activity can be detected by incubating the sample in a well that contains immobilized substrate, e.g., IGFBP-4. Substrate is specifically labeled, i.e., radioactively or non-radioactively. Upon proteolytic cleavage of the substrate, labeled fragments are liberated into the liquid phase and can be detected. Substrate can be immobilized, for example, by coating with antibodies or IGF-II.

Labeling can also be accomplished by using IGFBP-4 expressed with different tags on the N-terminus or C-terminus of the protein, for example an N-terminal FLAG tag and a C-terminal c-myc tag. This allows IGFBP-4 to be immobilized with a monoclonal antibody that binds one of these tags. Detection of bound IGFBP-4 can then be accomplished by standard ELISA methodology using, for example, a peroxidase conjugated monoclonal antibody that recognizes the other tag. IGFBP-4 can also be immobilized and detected using monoclonal antibodies that recognize the N-terminal and the C-terminal, respectively. Proteolytic activity will result in a decreased signal, dependent on the amount of proteinase activity and time of incubation.

Agents Altering PAPP-A Protease Activity

The invention also provides methods for identifying agents that alter the protease activity of PAPP-A. "Altered" refers to inhibiting or enhancing PAPP-A activity. As used herein, "agents" refers to a biological macromolecule such as an oligonucleotide or a peptide, a chemical compound, a mixture of chemical compounds, or an extract isolated from bacterial, plant, fungal or animal matter. Inhibiting agents are identified by incubating an isolated PAPP-A polypeptide, an activator of protease activity, and a substrate of PAPP-A with the agent, and determining if proteolysis of the substrate is inhibited. As used herein, an "isolated PAPP-A polypeptide" is separated from cellular components that naturally accompany it. Typically, the polypeptide is isolated when it is at least 60% (e.g. 70%, 80%, 90%, or 95%), by weight, free from proteins and naturally occurring organic molecules that are naturally associated with it. As used herein, "polypeptide" refers to a PAPP-A polypeptide of any length that has protease activity. Activators are identified in a similar manner, except that the standard activator, e.g, insulin-like growth factor I or II, is omitted from the reaction. IGFBP-4 or a fragment thereof, are particularly useful substrates of PAPP-A. Reactions for identifying inhibitors or activators are carried out as described above. The methods are suitable for screening large libraries of potential inhibitors or activators.

As PAPP-A binds to the cell surface, inhibiting or preventing binding of PAPP-A to the cell surface may be equivalent to inhibition of the proteolytic activity by interference with the active site of PAPP-A. Agents that inhibit or prevent the binding of PAPP-A to the cell surface can be identified using flow cytometry. In general, cells are incubated with a potential blocking agent, then contacted with a monoclonal antibody having specific binding affinity for PAPP-A, and binding to the cell surface is assessed with flow cytometry. Adhesion blocking agents include, for example, a monoclonal antibody or other polypeptide that binds to an epitope needed for binding to a cell-surface receptor.

Medical Devices

The invention also features a medical device for placement in a patient (e.g., an implant) that includes an agent that inhibits or activates PAPP-A protease activity. Suitable agents are readily identified using the methods described herein. The device can be impregnated with the agent or can be coated with the agent. Non-limiting examples of inhibitors include an antibody such as anti-PAPP-A polyclonal or monoclonal, or a metalloprotease inhibitor such as 1,10-phenanthroline. IGFBP-4 protease activity of PAPP-A is potently inhibited by 1,10-phenanthroline, but is not inhibited by tissue inhibitors of matrix metalloproteases (TIMP'S). Other inhibitors of the IGFBP-4 protease activity include small molecules such as derivatives of hydroxamic acid. Anti-PAPP-A/proMBP polyclonal IgG, but not non-specific rabbit IgG, also inhibits IGF-dependent IGFBP-4 protease activity in HFCM in a dose-dependent manner. In addition, polypeptides (i.e., any chain of amino acids, regardless of length or post-translational modification), including modified polypeptides, can function as inhibitors. For example, proMBP functions as an inhibitor of the IGFBP-4 protease activity of PAPP-A and can be used for coating or impregnating the medical device. Modified polypeptides include amino acid substitutions, deletions, or insertions in the amino acid sequence as compared with a corresponding wild-type sequence, as well as chemical modifications. Although protease-resistant IGFBP-4 is not an inhibitor per se of the IGFBP-4 protease activity of PAPP-A, similar results are expected when protease resistant IGFBP-4 is used for coating or impregnating a medical device.

For example, coating or impregnating the medical device with a PAPP-A inhibitor can help prevent the development of restenosis following balloon angioplasty, or can prevent a further increase in size of an atherosclerotic plaque. Coronary angioplasty with stent placement is currently the leading therapeutic approach for coronary atherosclerosis. An important goal of angioplasty of coronary artery disease is to prevent both acute and chronic complications. Modem procedures are quite successful in eliminating immediate problems. Unfortunately, restenosis still occurs in 20–30% of stented patients. No known pharmacological intervention is available to prevent the restenosis. Without being bound by a particular mechanism, it is thought that an increase in IGFBP-4 protease expression by coronary smooth muscle cells precedes neointimal formation in response to angioplasty in humans.

For example, enhanced PAPP-A activity can be useful for wound healing, fractures, osteoporosis, or ovulation. Osteoporosis or other conditions of bone loss may benefit from increased bone formation and decreased bone resorption. Agents that enhance PAPP-A activity can be, for example, a modified IGF, i.e., an IGF analog. Analogs include IGF polypeptides containing amino acid insertions, deletions or substitutions, as well as chemical modifications. Amino acid substitutions can include conservative and non-conservative amino acid substitutions. Conservative amino acid substitutions replace an amino acid with an amino acid of the same class, whereas non-conservative amino acid substitutions replace an amino acid with an amino acid of a different class. Non-conservative substitutions result in a change in the hydrophobicity of the polypeptide or in the bulk of a residue side chain. In addition, non-conservative substitutions can make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Amino acid insertions, deletions and substitutions can be made using random mutagenesis, site-directed mutagenesis or other recombinant techniques known in the art.

The medical device can be, for example, bone plates or bone screws that are used to stabilize bones, or a stent, which typically is used within the body to restore or maintain the patency of a body lumen. Blood vessels, for example, can become obstructed due to an atherosclerotic plaque that restricts the passage of blood. A stent typically has a tubular structure defining an inner channel that accommodates flow within the body lumen. The outer walls of the stent engage the inner walls of the body lumen. Positioning of a stent within an affected area can help prevent further occlusion of the body lumen and permit continued flow. A stent typically is deployed by percutaneous insertion of a catheter or guide wire that carries the stent. The stent ordinarily has an expandable structure. Upon delivery to the desired site, the stent can be expanded with a balloon mounted on the catheter. Alternatively, the stent may have a biased or elastic structure that is held within a sheath or other restraint in a compressed state. The stent expands voluntarily when the restraint is removed. In either case, the walls of the stent expand to engage the inner wall of the body lumen, and generally fix the stent in a desired position.

Pharmaceutical Compositions

Identification of PAPP-A as the IGFBP-4 protease provides methods for affecting growth and differentiation in vivo by using PAPP-A as a therapeutic target. Inhibitors of PAPP-A will decrease the amount of bioavailable IGF-I and IGF-II. For example, inhibition of PAPP-A activity can be useful in disorders such as restenosis, atherosclerosis, and fibrosis. Activators, or agents that increase the activity of PAPP-A, will increase the amount of bioavailable IGF-I and IGF-II.

Agents that alter PAPP-A activity or that alter adherence of PAPP-A to cell surfaces can be incorporated into pharmaceutical compositions. For example, an antibody such as anti-PAPP-A polyclonal or monoclonal, can be formulated into a pharmaceutical composition by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules: or for intranasal administration, particularly in the form of powders, nasal drops, or aerosols. Compositions for other routes of administration may be prepared as desired using standard methods.

Formulations for parenteral administration may contain as common excipients (i.e., pharmaceutically acceptable carriers) sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxyethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration The invention will be further described in the following examples, which do not limit the scope of the invention described in the claims.

EXAMPLES

Example 1

Identification of the IGFBP-4 Protease as PAPP-A

Human fibroblasts from a normal male donor (GM03652, Coriell Institute, Camden, N.J.) were grown to confluency in T65 flasks, washed twice with DMEM, and then changed to 15 ml of 50:50 Waymouth's medium:DMEM containing 100 units/ml penicillin. 100 g/ml streptomycin/4 mM glutamine/0.1% BSA and incubated for 6 hr at 37° C. The cells again were washed and changed to 10 ml of the serum-free medium and incubated for 72 hr at 37° C. Human fibroblast conditioned medium (HFCM) was placed in a sterile conical tube and centrifuged at 2,500 rpm for 30 min at 4° C. to remove cellular debris, decanted into another sterile conical tube, and stored at −30° C.

PAPP-A Activity. IGFBP-4 proteolysis was assayed by incubating the sample overnight at 37° C. with 2 mM $CaC_2$/50 mM Tris (pH 7.5)/10,000 cpm of $[^{125}I]$IGFBP-4 in the absence and presence of 5 nM IGF-II in a total volume of 25 μl. Proteins were separated by reducing 15% SDS/PAGE and visualized by autoradiography. For some experiments, PAPP-A polyclonal antibody or nonspecific rabbit IgG was added to the assay mixture or was used in conjunction with protein G plus protein A-agarose (Oncogene Science) to immunoprecipitate IGFBP-4 protease activity before assay.

PAPP-A Purification. HFCM (800 ml), in six 130- to 150-ml batches, were passed over a 25-ml bed volume of iminodiacetic acid immobilized to Sepharose 6B (Sigma) loaded with $Zn^{+2}$ and equilibrated with 50 mM Tris/50 mM NaCl, pH 7.4. Bound proteins were eluted sequentially with 50 ml each of a 0.5 pH unit stepwise decreasing gradient. The pH 5.0 fraction was immediately adjusted to pH 7.4 and passed over a 1-ml bed volume wheat germ agglutinin column equilibrated with 20 mM Tris/100 mM NaCl (pH 7.5) at 4° C. Bound proteins were eluted with 15 ml each of 50 mM Tris/100 mM NaCl (pH 7.5) alone and then with 25 mM and 500 mM N-acetylglucosamine. Five-ml fractions were collected and assayed for IGFBP-4 protease activity. Fractions from the six chromatography runs were pooled, concentrated by ultrafiltration, and electrophoresed through a 5% acrylamide SDS/PAGE gel under reducing conditions. The SDS/PAGE gel was silver stained, and four bands at 400, 230, 200, and 175 kDa that correlated to IGFBP-4 protease activity were excised for mass spectrometric analysis.

Excised bands were subjected to in-gel trypsin digestion. Soluble fragments were recovered from the digestion, then resolved and characterized by microcolumn high-performance liquid chromatography and automated tandem mass spectrometry. Microelectrospray columns were constructed from 360-μm o.d×100-μm i.d. fused silica capillary with the column tip tapered to a 5- to 10-μm opening. The microcolumns were packed with POROS 10 R2 (PerSeptive Biosystems, Framingham, Mass.) to a length of 10–15 cm. The mobile phase used for gradient elution consisted of (1) 0.5% acetic acid and (ii) acetonitrile/water 80:20 vol/vol containing 0.5% acetic acid. The gradient was linear from 0 to 40% over 30 min and from 40 to 60% over 5 min. The mass spectrometer used was a Finnigan-MAT (San Jose, Calif.) LCQ equipped with a microelectrospray ionization source. Tandem mass spectra were acquired during the entire gradient run automatically. The protein sequence and nucleotide sequence databases were searched directly with tandem mass spectra by using the computer program SEQUEST. Each sequence returned by SEQUEST was verified by inspecting the fit of the amino acid sequence to the corresponding tandem mass spectrum.

Following standard protocols, poly(A)-tailed mRNA (10 μg) was electrophoresed through a 1.5% agarose gel and transferred to nylon membrane (Hybond-N, Amersham Pharmacia). The membrane was pre-hybridized for 6 hr and then hybridized overnight at 43° C. with 107 cpm of $^{32}$P-labeled PAPP-A cDNA probe corresponding to nucleotide 10-2365 (GenBank accession no X68280). The membrane was washed three times, dried, and exposed to film.

Western Blotting. For Western analysis, samples were run on 8% Tris/tricine gels and blotted onto polyvinylidene difluroride membrane (Millipore). The membrane was blocked in 2% Tween 20 and washed with 5 mM Tris/500 mM NaCl/0.1% Tween 20/1% fetal bovine serum, pH 9.0. The blots were then incubated with monoclonal PAPP-A antibodies 234-2. Qin et al., *Clin. Chem.*, 1997, 43:2323–2332. The secondary antibodies were peroxidase-conjugated anti (mouse-IgG) P260 (Dako). Blots were developed by using enhanced chemiluminescence (ECL, Amersham).

ELISA. PAPP-A antigen was measured through a standard sandwich ELISA. The capture antibody was polyclonal anti-PAPP-A/proMBP, and detection was done with anti-PAPP-A monoclonal antibodies 234-2 and 234-5 followed by peroxidase-conjugated anti(mouse-IgG) P260. Highly purified PAPP-A/proMBP, prepared as described by Oxvig et al., *Biochim. Biophys. Acta,* 1994, 1201:415–423, was used for calibration.

Purification of the IGF-dependent IGFBP-4 protease was monitored with a specific bioassay, i.e., cell-free degradation, of $[^{125}I]$IGFBP-4 into 18- and 14-kDa radiolabeled fragments in the presence, but not the absence, of added IGF-II. This approach had the clear advantage of ensuring the purification of the specific enzyme of interest. Highly purified IGF-dependent IGFBP-4 protease was obtained from 800 mL of HFCM by a combination of zinc chelate and lectin affinity chromatography. Non- and weakly bound proteins came out in the flowthrough or were eluted with three washes of 0 mM and three washes of 25 mM N-acetylglucosamine. IGF-dependent IGFBP-4 protease activity was eluted with three washes of 500 mM N-acetylglucosamine. IGF-dependent IGFBP-4 protease activity was defined as the loss of intact 24 kD [$^{125}$I]IGFBP-4, and the appearance of 18- and 14-kDa radiolabeled fragment in the presence, but not in the absence, of 5 nM IGF-I.

The final fraction containing the IGF-dependent IGFBP-4 protease activity was further analyzed by SDS/PAGE, which revealed four high molecular mass bands at 400, 230, 200, and 175 kDa. The proteins in these bands were identified by tandem mass spectrometry microsequencing. All of the peptides represented known proteins or proteins deduced from known cDNA sequences. Peptides identified in the 175 kDa band included human α-2-macroglobulin, human thrombospondin 1, human collagen, bovine α-1-antichymotrypsin isoform pHHK1, human soares testis NHT cDNA clone 727252.5', sommer *Pristionchus pacificus*, human ribonuclease 6, and *Caenorhabditis elegans* cDNA clone yk 182d6. In the 200 kDa band, peptides identified included human PAPP-A, rat hemiferrin, and bovine transferrin. Human laminin γ-1 chain and human laminin β-chain were identified in the 230 kD band, and human collagen α-1 was identified in the 400 kD band.

An extensive literature search involving a comparison of the characteristics of the IGF-dependent IGFBP-4 protease from HFCM and the proteins identified by tandem mass spectrometry revealed only one match. This candidate protein was PAPP-A. Peptides identified for PAPP-A included residues 110–116 (ADLELPR, SEQ ID NO:1), 133–143 (SPAVITGLYDK, SEQ ID NO:2), 190–209 (SYLPGQWVYLAATYDGQFMK, SEQ ID NO:3), 373–387 (EQVDFQHHQLAEAFK, SEQ ID NO:4), 1071–1087 (TISYPYSOLAQTTFWLR, SEQ ID NO:5), and 1180–1195 (SFDNFDPVTLSSCQRG, SEQ ID NO:6). PAPP-A is one of four proteins originally isolated from normal human pregnancy serum. Lin et al., *Am. J. Obstet. Gynecol.*, 1974, 118:223–236. PAPP-A has been used as an index of placental function and a first-trimester screen for Down's Syndrome. In addition, placental PAPP-A "knockout" in humans appears to be associated with Cornelia de Lange syndrome, a condition involving incomplete fetal development and subsequent deformities. PAPP-A and the IGF-dependent IGFBP-4 protease from HFCM are similar in that they are both high molecular weight glycosylated proteins that bind $Zn^{2+}$. Furthermore, amino acid sequence derived from cloned cDNA encoding PAPP-A reveals a specific $Zn^{2+}$ binding motif (HEXXHXXGXXH, SEQ ID NO:7) at position 482–492 and a Met-turn further C-terminal found only in the metzincin family of metalloproteases. PAPP-A does not conform to other defining features of the individual metzincin superfamily members, and interestingly, in PAPP-A the linear distance between the zinc binding motif and the conserved Met-residue is 63 amino acids, whereas in other metzincins this distance is between 7 and 44 residues.

Figure 1B:
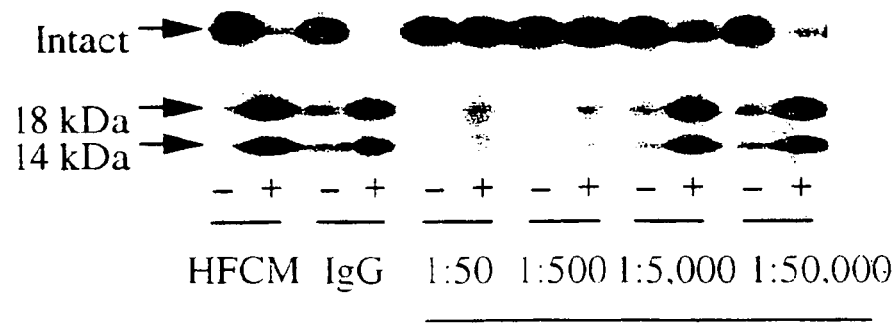
Figure 1C:
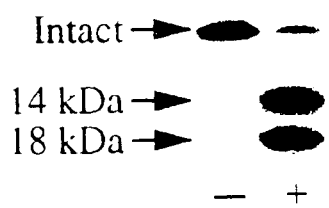

Identification of the IGF-dependent IGFBP-4 protease as PAPP-A was verified with further biochemical analyses. Anti-PAPP-A/proMBP polyclonal IgG, but not nonspecific rabbit IgG, inhibited IGF-dependent IGFBP-4 protease activity in HFCM in a dose-dependent manner (FIG. 1A). At a 1:50 titer of anti-PAPP-A/proMBP polyclonal antibody, IGFBP-4 proteolysis was completely inhibited; a 1:500 titer inhibited 84% of the protease activity, whereas a 1:5,000 titer inhibited 15% of IGF-induced IGFBP-4 protease activity in these cell-free assays. In other experiments, anti-PAPP-A/proMBP polyclonal IgQs were used to immunodeplete specifically and completely IGFBP-4 protease activity from the medium (FIG. 1B). Moreover, PAPP-A/proMBP that had been purified from serum of pregnant women exhibited IGF-dependent IGFBP-4 protease activity (FIG. 1C). In a cell-free assay, PAPP-A/proMBP alone had no effect on [$^{125}$I]IGFBP-4, but addition of IGF-II initiated proteolysis into radiolabeled fragments of 18 and 14 kDa, identical to what is seen with HFCM. Similar results were obtained with four different preparations of highly purified PAPP-A/proMBP.

PAPP-A is most highly expressed in the syncytiotrophoblast of the placenta, which is the main source of circulating PAPP-A in pregnancy. Bonne et al., *Lab. Invest.*, 1994, 71:560–566. PAPP-A, however, has been detected in serum from nonpregnant as well as pregnant women and in preovulatory follicular fluid and has been immunolocalized to secretory endometrium, vascular endothelium, and actively proliferating fetal and adult tissues when polyclonal antisera, which reacts with both PAPP-A and proMBP, and to an unknown extent with other proteins, was used.

Northern and Western analysis was performed to demonstrate unequivocal PAPP-A expression in cultured human fibroblasts and bone cells. For Northern analysis, poly-A tailed mRNAs (10 μg) from cultured human cells were probed with $^{32}$P-labeled PAPP-A cDNA. Human cells that were tested included adult fibroblasts, adult osteoblasts, total osteoblasts, marrow stromal cells, MG63 osteosarcoma cells, U2 osteosarcoma cells, and TE85 osteosarcoma cells. Based on these experiments, it was observed that human fibroblasts expressed PAPP-A transcripts at −13 and 8.5 kB. The results from Northern blotting also show PAPP-A mRNA expression by normal human osteoblasts from adult and fetal sources and by osteoprogenitor cells, but not by several osteosarcoma cell lines. These findings are in agreement with those of previous studies showing IGF-dependent IGFBP-4 protease activity in medium conditioned by normal human osteoblasts, but not by transformed osteoblastic cells. Durham et al., *Endocrinology*, 1995, 80:987–993. Not only is PAPP-A mRNA expressed by human fibroblasts, PAPP-A protein is, in fact, secreted by cultured human fibroblasts. By ELISA, HFCM was found to contain 0.18±0.021 μg/ml PAPP-A (n=4). For comparison, term pregnancy serum contains approximately 25 μg/ml PAPP-A. Western immunoblots were performed using HFCM (10 μl of 30× concentrate corresponding to 0.05 μg PAPP-A by ELISA) and PAPP-A/proMBP purified from pregnancy serum (0.05 μg). The proteins were separated by SDS/PAGE under both nonreducing and reducing conditions, transferred to membrane, and immunoblotted with PAPP-A-specific monoclonal antibodies.

Western blotting analysis showed that HFCM reacted with monoclonal antibodies specific for PAPP-A. In nonreducing SDS/PAGE, PAPP-A from HFCM migrates with a molecular mass of 400 kDa, somewhat faster than PAPP-A/proMBP isolated from pregnancy serum but slower than PAPP-A monomer seen at 200 kDa in reducing SDS/PAGE. Expression of proMBP by fibroblasts was not detected by ELISA, Western or Northern blotting. Thus, PAPP-A in HFCM forms monomers.

Example 2

Expression of PAPP-A in Reproductive and Non-Reproductive Tissues

Term placental tissue (outer maternal side) from cesarean sections was provided by the Department of Gynecology and Obstetrics, Aarhus University Hospital. First trimester trophoblast tissue was from the Danish Cancer Society, Aarhus. Prostate tissue from hyperplasies and adenocarcinomas was provided by the Department of Experimental Clinical Oncology, Aarhus University Hospital. Mononuclear cells from bone marrow, prepared as described, were obtained from the Department of Hematology, Aarhus County Hospital, Denmark. Normal breast tissue, and samples from lobular and ductal breast carcinomas were provided by the Department of Pathology, Aarhus County Hospital, Denmark. Samples from ovary, endometrium, myometrium, and tuba uterina, provided by the Department of Gynecology and Obstetrics, Aarhus University Hospital, were from hysterectomies from normal postmenopausal women (age <50 years). A blood sample was drawn from a pregnant woman (first trimester). All tissue samples were stored in liquid nitrogen.

Extraction of mRNA and cDNA Synthesis. Frozen tissue samples were pulverized using a mortar embedded in dry ice. Approximately 20 mg tissue powder or 106 cells were then lysed in 1 ml lysis/binding buffer (0.5 M LiCl, 10 mM EDTA, 5 mM dithiothreitol, 1% SDS, 100 mM Tris-HCl, pH 8,0) using a glass homogenisator (Wheaton, USA). Poly-A+ RNA was isolated using the Dynabeads mRNA DIRECT kit (Dynal A/S, Norway), according to manufacturer's instructions. Poly-A+ RNA was eluted from the oligo-dT Dynabeads by incubation in 20 µl 2 mM EDTA for 2 min at 65° C. First strand cDNA was synthesized immediately hereafter by incubating 50% of the eluted Poly-A+-RNA for 60 min at 42° C. with 4 units avian myeloblastosis virus reverse transcriptase, 10 pmol oligo-dT24 1 pmol 5'AAAC-CCATTTTATTGCAGGGAGG-3' (MBP specific primer (nt 840–818 in the proMBP cDNA sequence, SEQ ID NO:8), 1 pmol 5'-CTGTGGTTGTGTGACAAATGGC-3' (PAPP-A specific primer (nt 4936–4915 in the PAPP-A cDNA sequence, SEQ ID NO:9), 40 units RNAsin, 1 mM dNTP, and 5 mM $Mg^{2+}$, in 20 µl of the supplied buffer. All reagents except primers, were from Promega. The remaining Poly-A+3 RNA was processed in parallel without addition of reverse transcriptase. The resulting cDNA was diluted (1:44, n=1 to 10) in dd$H_2O$, and used directly as template for competitive PCR, or stored at −20° C. until use.

Preparation of Internal Standard Templates. The internal standard (IS) is a deletion variant of the respective cDNA PCR product (FIG. 2) that can be amplified with the same primers as the cDNA. The PAPP-A IS was constructed by primer mediated deletion as previously described. Briefly, the 5'-CAGTCAGCTGCTCAACGGAAGGACTCA-CATTGG-3' (nt 4712–4731 and 4789–4805 in the PAPP-A cDNA sequence, SEQ ID NO:10) was used with 5'-GGAG-GCTCTGGGACTGCAC-3' (nt 4904–4886, SEQ ID NO:11) as primers in a PCR, using first strand cDNA from placenta as template, to make a 62 bp deletion variant of the PAPP-A cDNA PCR-product with the same primer binding sequences as the PAPP-A cDNA. An MBP IS was constructed by excision of a HinPII-MspI fragment (nt 447–522 in the proMBP cDNA sequence), resulting in a 76 bp deletion variant of the cDNA PCR product. The β-actin IS was constructed by excision of a HinPII-MspI fragment (nt 1045–1136 in the β-actin cDNA sequence), resulting in a 92 bp deletion variant. For construction of a glyceraldehyde-3-phosphate dehydrogenase (GAPDH) IS, the primer 5'-AACGGGAAGCTCACTGGCATGATGACAT-CAAGAAGGTGGTG-3' (nt 674–694 and 765–787 in the GAPDH cDNA sequence, SEQ ID NO:12) was used with 5'-CCACCACCCTGATGCTGTAGC-3' (nt 977–957, SEQ ID NO:13) in a PCR using first strand cDNA as template to make a 73 bp deletion variant of the GAPDH PCR-product with the same primer binding sequences as the cDNA PCR-product. The ISs were purified from agarose gels and verified by sequence analysis. The fixed amount of IS added to each PCR was taken from the same batch stored in ready to use aliquots at −20° C.

Primers for Competitive Polymerase Chain Reaction. β-Actin: 5'-CACCCAGCACAATGAAGATCAAG-3' (nt 1003–1025, SEQ ID NO: 14) and 5'-GTCAAGAAAGGGT-GTAACGCAAC-3' (nt 1207–1185, SEQ ID NO: 15); PAPP-A: 5'-CAGTCAGCTGCTCAACGGAA-3' (nt 4712–4731, SEQ ID NO: 16) and 5'-GGAGGCTCTGG-GACTGCAC-3' (nt 4904–4886, SEQ ID NO: 17); MBP: 5'-TTAGTCAAGCTTGGTTTACTRGC-3' (nt 423–445, SEQ ID NO: 18) and 5'-GGAAGTCTTCTGAG-GCAGTGG-3' (nt 720–700, SEQ ID NO:19); GAPDH: 5'-AACGGGAAGCTCACTGGCATG-3' (nt 674–694, SEQ ID NO:20) and 5'-CCACCACCCTGTTGCTGTAGC-3' (nt 977–957, SEQ ID NO:21). Numbers in parentheses refer to the positions in the corresponding cDNA sequences. Gene and cDNA sequences were obtained from Genbank (accession numbers: GAPDH: J02642 and J04038; β-actin: X00351 and M10277; MBP: X14088 and M34462; PAPP-A: X68280). All primers were from DNA Technology, Aarhus, Denmark.

Figure 2:
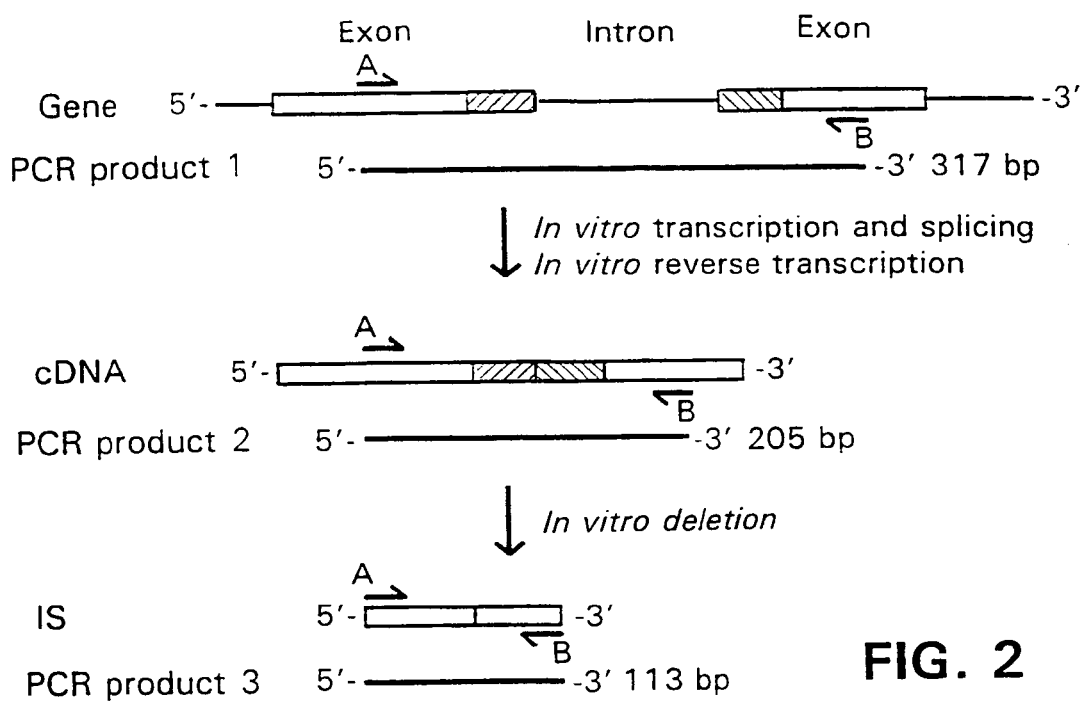
FIG. 2 is a schematic that compares amplification products. Lengths of the PCR products with genomic DNA (product 1), cDNA (product 2), or internal standard (IS, product 3) as template are indicated for β-actin. As there is a substantial difference in the product sizes between PCR product 1 and 2, contamination with genomic DNA in the mRNA preparation can be easily detected. A and B represent the 5'- and 3'-competitive PCR primers, respectively. Boxes represent exons in genomic DNA or cDNA. Shaded boxes represent the part of the cDNA that is deleted to generate the IS, either by excision of a restriction fragment or by primer mediated deletion.

Competitive Polymerase Chain Reaction. All PCRs were performed in a total volume of 50 µl with 1.5 unit SuperTaq (HT Biotechnology, UK). 0.25 nM dNTP (Pharmacia, Sweden), 80 pmol of each primer, 1×SuperTaq buffer, 1 µl internal standard template (except blank control) in glass tubes using an Abacus thermal cycler (Denzyme, Denmark) with a ramp rate of 4° C./s. Diluted aliquots of all reagents (stored at −20° C.) were used to prepare a reaction mixture of which 49 µwas pipetted to each tube in a series of PCR experiments. One series includes reactions with a dilution series of first-strand cDNA from one tissue, a dilution series from another tissue, one control with IS as the only template, and one blank control (which is taken from the master PCR-mixture before addition of the IS). After addition of 1 µl diluted cDNA template, 37 cycles of PCR were performed using the following parameters: 94° C. for 30 s (90 s in the first cycle), annealing for 30 s (vide infra), 72° C. for 40 s (400 s in the last cycle). Annealing temperatures were 62° C. for β-actin and GAPDH, 60° C. for PAPP-A, and 58° C. for MBP. The amount of IS template, was in a linear region of the double logarithmic plot of the PCR product as a function of the dilution factor. This ensures that the amplifications were in the exponential phase throughout the 37 cycles. The PCR primers in each primer-pair were positioned on different exons enabling an easy detection of possible genomic DNA contamination (FIG. 2 and Table 1). No genomic DNA contamination of the cDNA preparations were observed in any of the tissues examined.

TABLE 1

Size of PCR-products of the indicated templates in base pairs

| Template | Genomic DNA | cDNA | Internal Standard |
|---|---|---|---|
| β-actin | 317 | 205 | 113 |
| GAPDH | 1529 | 304 | 231 |
| PAPP-A | nd[a] | 189 | 127 |
| MBP | 408[b] | 298 | 222 |

[a] The intron/exon structure is not determined for PAPP-A.
[b] The 5'-primer used spans an intron.

Figure 3:
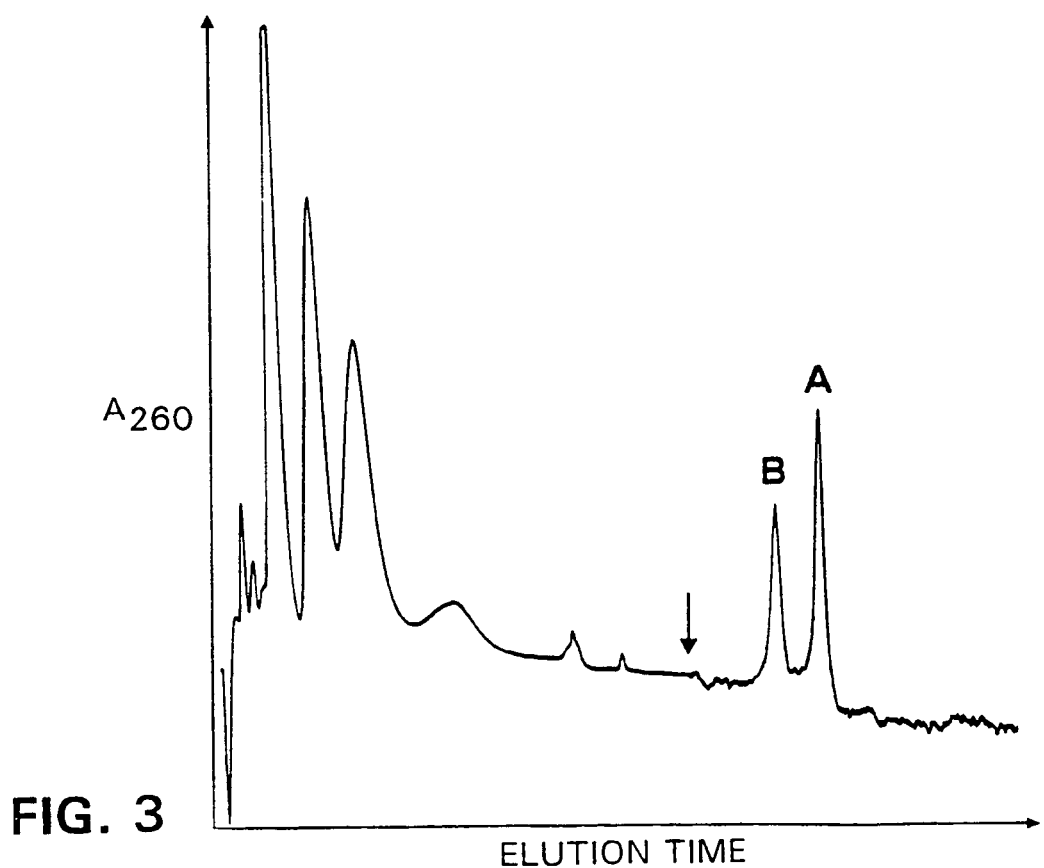
FIG. 3 is the $A_{260}$ elution profile from ion exchange chromatography separation of PCR products with PAPP-A specific primers. Buffer components, dNTPs, and primers elute first. The PCR products of cDNA (A) and internal standard (B) templates are well separated and can easily be quantified. The vertical arrow denotes change of scale (8 fold increase in sensitivity).

Quantification. For each dilution series, the two samples with about equal amounts of cDNA and IS PCR-products, as judged by gel-electrophoresis in a 2.5% agarose gel, were separated on a Hewlett-Packard 1084 HPLC instrument equipped with a Waters Gen-Pak4,41 J FAX nonporous ion-exchange column using a 20 min. linear gradient from 0.3 to 0.7 M NaCl in TE buffer, pH 7.5 at 60° C. (FIG. 3). The dilution, DIeq, that would have resulted in equimolar amounts of cDNA and IS PCR products, was calculated from equation 1, as described above.

A DIeq value was determined for each of the gene products as the mean value obtained from PCR of two independent dilution series and from two cDNA dilutions in each series. Finally, the specific abundance of PAPP-A or proMBP mRNA, Ax, was determined from equation 2, as described above.

Thus, the specific abundance is a measure of the mRNA level of the gene of interest, normalized against a measure of the total mRNA in the sample. Given a constant amount of β-actin mRNA molecules per cell, which is a reasonable assumption, the specific abundance, A, is independent of the amount of tissue used.

RNA Dot Blot Analysis. A $^{32}$P-labeled PAPP-A cDNA fragment pPa-1 and a $^{32}$P-labeled MBP PCR product (see above) was hybridized to a human RNA master blot (Clontech) following manufacturer's instructions. After washing twice with 0.15 M NaCl. 15 mM sodium citrate, 0.1% SDS, pH 7.0 at 65° C. for 30 min, autoradiography was performed for 24 h using a phosphorimager (Molecular Dynamics). The human RNA master blot contains samples from 50 different tissues spotted on the membrane, in addition to control DNA samples, including: whole brain; amygdala; caudate nucleus; cerebellum: cerebral cortex; frontal lobe; hippocampus; medulla oblongata; occipital pole; putamen: substantia nigra; temporal lobe; thalamus; subthalamic nucleus; spinal cord; heart: aorta: skeletal muscle; colon; bladder: uterus; prostate; stomach; testis; ovary; pancreas; pituitary gland; adrenal gland; thyroid gland: salivary gland; mammary gland; kidney; liver; small intestine; spleen: thymus; peripheral leukocyte; lymph node; bone marrow; appendix; lung; trachea; placenta; fetal brain; fetal heart, fetal kidney; fetal liver; fetal spleen; fetal thymus; fetal lung; yeast total RNA; yeast tRNA, E. coli rRNA; E. coli DNA; Poly r(A); human genomic repeat DNA; and human DNA. RNA amounts from all tissues were normalized against eight different housekeeping gene transcripts on the master blot.

Messenger RNA was extracted from frozen, homogenized tissue samples using oligo-dT coupled magnetic beads. This is a fast and easy protocol ensuring minimal degradation. To increase the sensitivity, both proMBP, PAPP-A, and oligo-dT specific primers were used in the first strand cDNA synthesis. Serial dilutions were made with the pool of cDNA obtained from the reverse transcription reaction. These cDNA dilutions were used as templates in competitive PCRs, with fixed amounts of gene specific IS template added. From measurements of the β-actin mRNA levels, the specific abundance was calculated for each tissue as detailed above. Levels of glyceraldehyde-3-phosphate dehydrogenase (GAPDH) mRNA also were measured. As expected, the specific abundance of GAPDH mRNA showed minimal variation (128±58 SD). This validates normalization against β-actin mRNA.

Figure 4:
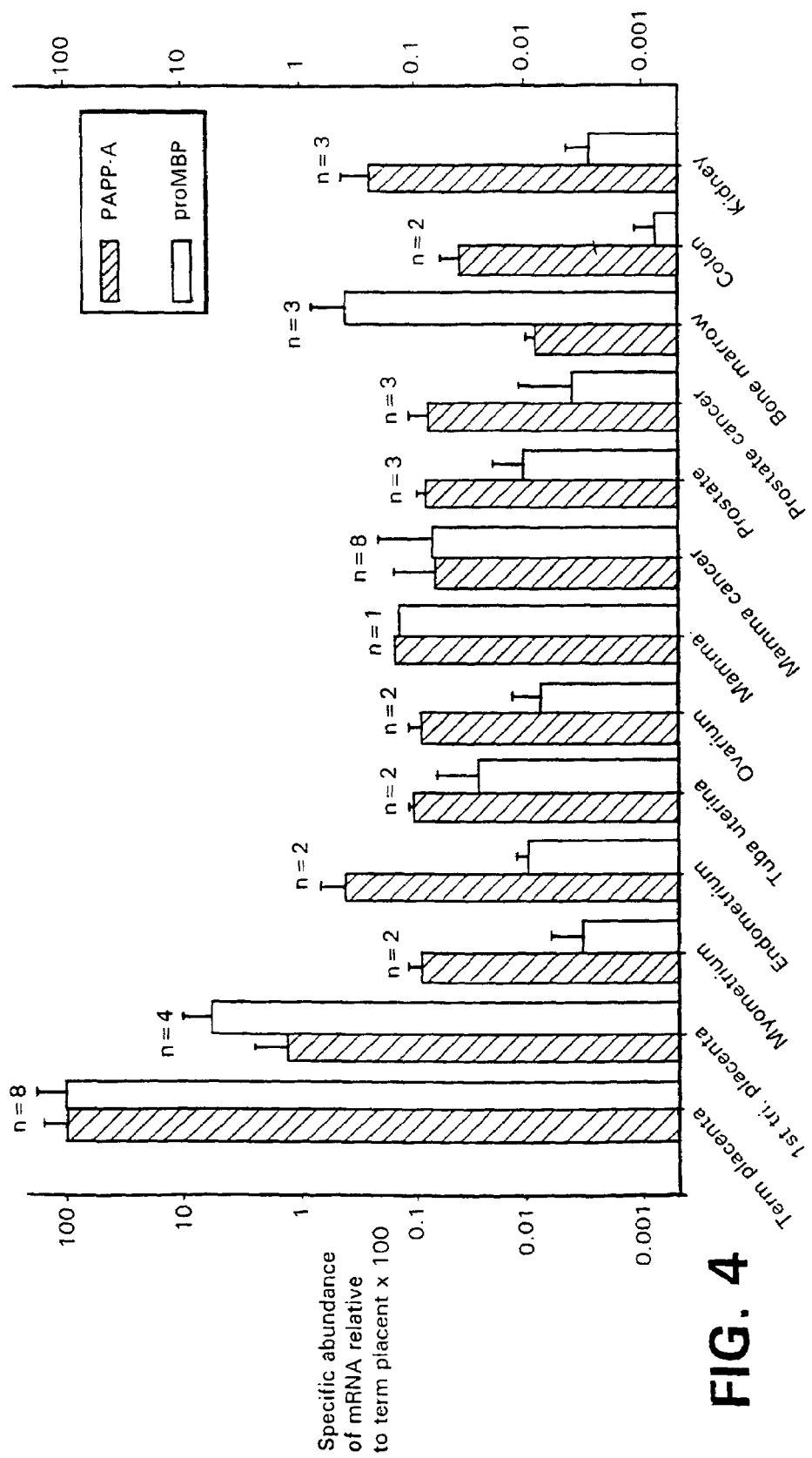
FIG. 4 is a histogram that indicates the specific abundances of PAPP-A and proMBP mRNA in tissues tested, normalized against the average term placenta specific abundance. Standard deviations are shown as error bars. The number of samples for each tissue is indicated above the columns.

The specific abundance of PAPP-A and proMBP mRNA in a total of 43 samples from 13 different tissues was measured using the semi-quantitative RT-PCR method described above. The results are summarized in FIG. 4, where the mean specific mRNA abundance for each tissue is shown relative to the specific abundance in term placenta, which contained the highest level measured for both PAPP-A and proMBP. Tissues assessed included term placenta, first trimester placenta, myometrium, endometrium, tuba uterina, ovarium, mamma, mamma cancer, prostate, prostate cancer, bone marrow, colon, and kidney. The specific abundance of PAPP-A and proMBP mRNA was dramatically lower in first trimester placenta than in term placenta (75 and 17 fold respectively). It is also evidence that all tissues examined contained measurable amounts of both mRNA species (FIG. 4). In endometrium from post menopausal women, the PAPP-A mRNA level was 250 fold lower than in term placenta. Most other tissues examined had a specific PAPP-A mRNA abundance 500 to 3000 fold lower than term placenta. In bone marrow cells, where proMBP mRNA was expected at a relatively high level, the specific proMBP mRNA abundance was 230 fold lower than in term placenta. In breast tissue, it was 800 fold lower than in term placenta, whereas the proMBP mRNA abundance was more than 1300 fold lower than term placenta in all other tissues tested.

Analysis of the mRNA in 1.5 ml whole blood, drawn from a pregnant woman, showed a very low β-actin mRNA level, and no detectable PAPP-A or proMBP mRNA. Thus, blood present in tissue samples cannot interfere with the measurements of the specific abundances of mRNA species.

In addition to the tissue samples analyzed by semi quantitative RT-PCR, a rapid screen for tissues producing high amounts of PAPP-A or proMBP mRNA was carried out. This was done by hybridizing a specific $^{32}$P-labeled PAPP-A (pPA-1) or proMBP cDNA probe to a membrane containing RNA from 50 different human tissues.

As expected, placenta showed a very high signal for both mRNA species. The only other tissue with a PAPP-A signal above background was kidney. With this method, proMBP mRNA was detected in placenta, bone marrow, and at very low levels in kidney.

Example 3

Figure 5:
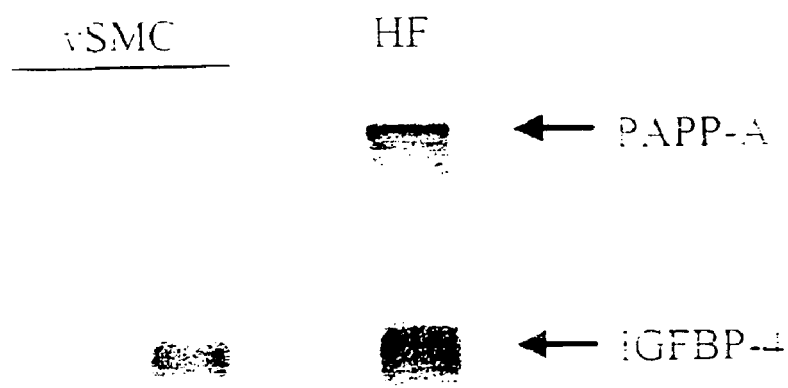
FIG. 5 is an autoradiogram of poly A+-enriched RNA from cultured porcine vascular smooth muscle cells (vSMC) and human skin fibroblasts (HF) probed for IGFBP-4 protease/PAPP-A and IGFBP-4 expression.

PAPP-A Expression in Porcine Smooth Muscle and in a Pig coronary Restenosis Model PolyA+-enriched mRNA of cultured-porcine vascular smooth muscle cells (vSMC) and human skin fibroblasts (HF) were probed for PAPP-A and IGFBP-4 expression. As indicated in FIG. 5, PAPP-A mRNA and its substrate, IGFBP-4 were expressed in vSMC.

IGF-dependent IGFBP4 protease activity also was detected in cell-conditioned medium from vSMC and HF. Protease activity was monitored in a cell-free assay, as described in Example 1, using [$^{125}$I]IGFBP-4 with, and without, IGF-II for 6 hours. Reaction products were analyzed by SDS-PAGE and autoradiography. Vascular smooth muscle cells secrete a protease identical to PAPP-A.

PAPP-A protein also was detected in vascular tissue in vivo, particularly endothelial cells and smooth muscle cells of the neointima 7 days post-balloon injury of pig coronary arteries. Oversize balloon angioplasty was performed in juvenile female pigs to stimulate neointimal hyperplasia. Schwartz, R. S. et al., Circulation, 82:2190–2200, 1990. Oversized balloon angioplasty and stent implantation was performed in immature female pigs (Sus scrofa). All animals receive 650 mg aspirin +250 mg Clopidogrel and 120 mg Isoptin-SRR 24 hours prior to surgery to reduce acute mortality due to platelet aggregation and coronary spasm. An arteriotomy was performed in standard surgical fashion and an introducer sheath was placed in the carotid artery. Heparin (200 units/kg) was administered through the sheath to maintain an activated clotting time (ACT)>300. A guiding-catheter was then placed into the sheath and advanced as needed under fluoroscopic guidance into the coronary arteries. A 0.014 guide wire was used to deliver devices to the predetermined sites. Immediately following placement of the stents, intravascular ultrasound was performed to document stent expansion and apposition characteristics, as well as to measure vessel diameter. The catheters were then removed, stent deployment characteristics noted, the arterial cutdown site repaired, and the animal allowed to recover. At sacrifice, animals were euthanized with an overdose of a commercial intravenous barbiturate (Sleepaway, 10 ml by ear vein). The heart was removed and placed in a cold physiologic solution (Kreb's Ringers). The coronary arteries were excised and cut into rings, and sections fixed by immersion in 4% paraformaldehyde in $NaPO_4$ buffer (pH 7.4). Then sections are embedded in paraffin and sliced into 3 mm cross sections from normal artery through injury and back into normal artery. Sections were stained with hematoxylin and eosin (H&E), elastic Van Gieson, or kept frozen. The arterial injury severity induced by angioplasty was assessed according to the injury score by Schwartz et al., Circulation, 1990, 82:2190–2200.

Coronary arteries from uninjured and injured vessels 1, 7, 14, 28 and 90 days after the procedure were excised and embedded in paraffin. Monoclonal human IGFBP-4 protease (PAPP-A) antibody was used for immunohistochemical staining. Qin Q-P et al., Clin. Chem., 1997, 43:2323–2332. The cells of the media layer and neointima showed strong immunostaining for IGFBP-4 protease at 7 days with peak expression 28 days after angioplasty. No staining was detected at day 1 and minimal staining was observed at day 90. No IGFBP-4 protease staining was apparent in uninjured sections. Using commercially available antibodies, IGFBP-4 staining was low and diffuse, and there was no specific staining for IGFBP-5. PAPP-A was detected by PAPP-A mouse monoclonal antibody (234–5), biotinylated secondary anti-mouse IgG, and streptavidin-horseradish peroxidase. Color was developed with 3-amino-9-ethylcarbazole substrate.

Example 4

Expression of Recombinant PAPP-A

This example describes the expression of recombinant PAPP-A (rPAPP-A) in mammalian cells. This represents an important attainment for the further study of the role of PAPP-A in the IGF/IGFBP system, and for the study of PAPP-A as a unique metalloproteinase. Of interest, a comparison between rPAPP-A and PAPP-A/proMBP complex from pregnancy serum revealed a pronounced difference in proteolytic activity. Based on these studies, it is believed that proMBP functions as a proteinase inhibitor in vivo. This finding establishes a biological role of proMBP outside the eosinophil leukocyte. It also represents a novel mode of proteinase inhibition with the enzyme covalently bound by disulfide bonds to its inhibitor.

Plasmid Construction. A PAPP-A expression plasmid was constructed from three overlapping partial PAPP-A cDNA clones, p29-2, pPA3, and pPA1. Kristensen, T. et al., Biochemistry, 1994, 33:1592–1598, Haaning, J. et al., Eur. J. Biochem., 1996, 237(1): 159–63. The Bbel-EcoRI fragment of p29-2, encoding PAPP-A residues 6–228 (with the N-terminal Glu residue being residue 1 and the cDNA sequence numbered with the codon encoding Glu-1 (GAG) as nucleotides 1–3), was excised by partial and full digestion, respectively, and ligated to a nucleotide fragment encoding an artificial signal peptide (MKDSCITVMAMALLSGFFF-FAPASSYAA, SEQ ID NO:22) plus residues 1–5 of PAPP-A. In brief, this latter fragment was generated in a PCR using a mixture of overlapping oligonucleotides (5'-CCTGCAT-CACTGTGATGGCCATGGCGCTGC-3' (SEQ ID NO:23), 5'-TGTCTGGGTTCTTTTCTTCGCGCCGGCCTC-3' (SEQ ID NO:24), 5'-GAGCTATGCCGCG-GAAGCTAGGGGCGCCAT-3' (SEQ ID NO:25), and 5'-GCGGCATAGCTCGAGGCCGGCGCGAAGAAA-3' (SEQ ID NO:26), 5'-AAGAACCCAGACAGCAGCGC-CATGGCCATC-3' (SEQ ID NO:27), 5'-ACAGTGATG-CAGGAATCCTTCATAAGCTTAG-3' (SEQ ID NO:28)) as a template, and primers containing a HindIII (5'-CTAAGCT-TATGAAGGATT-3', SEQ ID NO:29) and a BbeI (5'-ATG-GCGCCCTAGCTTCC-3', SEQ ID NO:30) recognition site. The ligation product was cloned into the HindIII/EcoRI sites of pBluescript II (Stratagene) to generate pBN-228. The EcoRI-ClaI fragment of pPA3, encoding PAPP-A residues 229–784, was excised and ligated to the HindIII-EcoRI fragment of pBN-228, and cloned into the HindIII/ClaI sites of pBluescript II to generate pBN-784. Further, the ClaI-EcoRI fragment of pPA1, encoding PAPP-A residues 785–1547 and containing part of the 3'UTR, was excised and ligated to the HindIII-ClaI fragment of pBN-784, and cloned into the HindIII/EcoRI sites of pBluescript II to generate pBN-1547. Because the ClaI site in the PAPP-A cDNA is sensitive to methylation, plasmids were propagated in an E. coli dam-strain when required.

Finally, the HindIII-XbaI fragment of pBN-1547, encoding the artificial signal peptide plus PAPP-A residues 1–1547, was cloned into the HindIII/XbaI sites of the mammalian expression vector pcDNA3.1+ (Invitrogen) to generate pcDNA3.1-PAPP-A. This construct was verified by sequence analysis. To allow for selection with hygromycin B (Invitrogen), the HindIII-XbaI fragment of pcDNA3.1-PAPP-A was excised and cloned into pcDNA3.1/Hygro(+) (Invitrogen) to obtain pcDNA3.1/Hygro-PAPP-A for generation of stably transfected cells. Plasmid DNA for transfection was prepared with QIAprep Spin Kit (Qiagen).

A deviation from the published PAPP-A cDNA sequence was found at one site: Nucleotides 78–80 (AGT) were not present, resulting in the absence of Val-27. In the original cDNA clones (p29-2 and pPA3) the same deviation was observed upon resequencing.

Tissue Culture, Transfection, and Protein Expression: Human embryonic kidney 293T cells (293tsA1609neo) were maintained in high glucose DMEM medium supplemented with 10% fetal bovine serum, 2 mM glutamine, nonessential amino acids, and gentamicin (Life Technologies). Cells were plated onto 6 cm tissue culture dishes, and were transfected 18 h later by calcium phosphate coprecipitation using 10 μg of DNA (pcDNA3.1-PAPP-A). After a further 48 h, the supernatants were harvested and cleared by centrifugation. For generating 293T cell lines that stably express PAPP-A, cells were transfected with FspI-linearized pcDNA3.1/Hygro-PAPP-A by the same method, selected for resistance to 400 μg/ml hygromycin B (Invitrogen). Single colonies were picked and expanded, and stable cell lines were maintained in medium with 100 μg/ml hygromycin B. COS-7 cells were maintained in the same medium, but transfected with SuperFect (Qiagen) according to the manufacturer's protocol.

Two days post transfection the supernatant contained around 5 μg/ml of recombinant PAPP-A (rPAPP-A) as measured by a PAPP-A specific ELISA. PAPP-A was not detectable in supernatants from mock transfected cells. The rPAPP-A antigen was recognized in ELISA by all monoclonal antibodies available, and the integrity of the protein was verified by Western blotting. Similar results were obtained with transfected COS-7 cells.

ELISA: Levels of recombinant PAPP-A in the supernatants were measured by a standard sandwich ELISA. PAPP-A polyclonal antibodies, anti(PAPP-A/proMBP), were used for capture, and a PAPP-A monoclonal antibody (mAb) (234–2.234–5, 234–4, 234-6, 234-3, or 234-7) followed by peroxidase conjugated anti(mouse IgG) (P260, DAKO) for detection. PAPP-A/proMBP purified from pregnancy serum or purified rPAPP-A was used to establish standard curves. See Qin, Q. P. et al., Clin. Chem., 1997, 43:2323–2332. The amount of protein in the standards was determined by amino acid analysis.

Protein Fractionation: Purification of rPAPP-A from cell culture supernatants was accomplished by a procedure of precipitation, heparin chromatography, and gel filtration. Protocols for purification of PAPP-A/proMBP complex from pregnancy serum were not useful for purification of rPAPP-A due to differences in precipitation with PEG (16% for proMBP/PAPP-A complex vs. 4–12% for rPAPP-A). Recombinant PAPP-A was precipitated essentially quantitatively from cell culture supernatants (50 ml) by 10% (w/v) PEG 6000. The precipitate was dissolved in 50 mM Tris. 50 mM NaCl, pH 8.0 containing standard protease inhibitors and loaded onto a HiTrap Heparin Sepharose (5 ml) (Pharmacia) equilibrated with the same buffer. Bound proteins were eluted by a linear increase in the salt concentration to 1000 mM over 30 min at 1 ml/min. Recombinant PAPP-A eluted mainly as a single peak around 600 mM NaCl. Finally, pooled fractions were concentrated by ultrafiltration and chromatographed at 0.5 ml/min on a Superose 6 HR 10/30 (Pharmacia) equilibrated with PBS. PAPP-A/proMBP was purified from term pregnancy serum as previously described by Oxvig. C. et al., Biochem. Biophys. Acta. 1994, 1201:415–423.

Figure 6B:
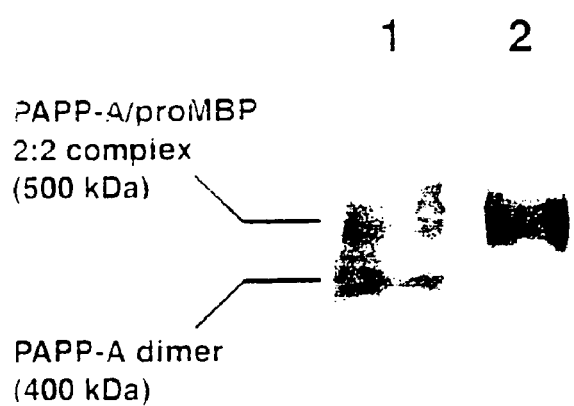
FIGS. 6A–6B are an anion exchange chromatogram and a Western blot of selected fractions, respectively.
Figure 6A:
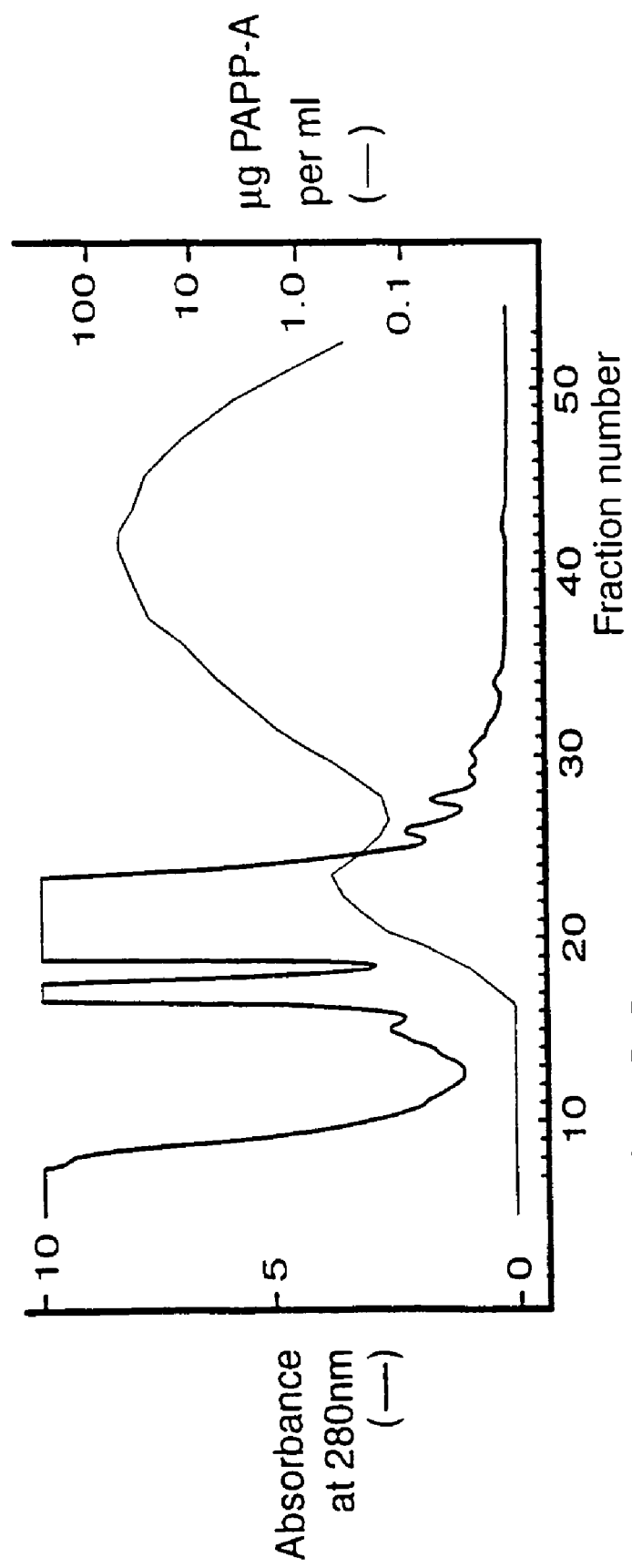

For analytical purposes pooled pregnancy serum, pregnancy plasma, or culture supernatant was run on a Mono Q HR 10/10 (Pharmacia) equilibrated with 50 mM Tris, 50 mM NaCl, pH 8.0. Prior to column loading, samples were diluted by addition of two volumes of water. Elution was performed with a linear salt gradient from 50 mM to 1000 mM over 40 min at 1 ml/min, and fractions of 1 ml were collected. For all runs, the salt concentration was 50 mM in fraction 10 and 1000 mM in fraction 50 (FIG. 6A). The absorbance at 280 nm was recorded in a second run of 1/10 of the same serum, and multiplied by a factor of ten. The two chromatograms obtained were superimposable, and the shape and position of the larger PAPP-A peak (around fraction 43) was the same. The smaller PAPP-A peak (around fraction 24) also had the same position in the two runs, but with the ELISA used, the levels of PAPP-A antigen could not be determined accurately in those fractions from the second run. Thus, ELISA values of the first run are used.

Miscellaneous Procedures SDS-PAGE was performed in Tris-glycine gels (10–20% or 15%) or in precast 3–8% Tris-acetate gels (Novex). Separated proteins were visualized by Coomassie-staining of gels, or first blotted onto a PVDF membrane for sequence analysis on an Applied Biosystems 477A sequencer equipped with an on-line HPLC. Immunovisualization was performed as in Example 2 using enhanced chemiluminescence. Blots were blocked with 2% Tween 20 and equilibrated in 50 mM Tris, 500 mM NaCl, 0.1% Tween 20, pH 9.0 (TST). Primary antibody (mAb 234-2 for PAPP-A, and mAb 234-10 for proMBP) was diluted in TST containing 0.5% fetal bovine serum, and blots were incubated for 1 h at 37° C. Incubation with peroxidase-conjugated secondary antibodies (P260, DAKO) diluted in TST was done for 1 h at room temperature. Hydrolysis and quantification of amino acids and amino sugars was carried out as previously described by Oxvig et al., Biochim. Biophys Acta, 1994, 1201:415–423.

Measurement of PAPP-A Proteolytic Activity: IGFBP-4 proteolysis was assayed as described in Example 1. The activity of the PAPP-A/proMBP complex was compared to the activity of rPAPP-A in two parallel time course experiments scaled up to larger reaction volumes: Equal amounts of sample A (pool of pregnancy serum diluted to 7 μg/ml of PAPP-A/proMBP as determined by ELISA calibrated with purified PAPP-A/proMBP) and sample B (as sample A, but rPAPP-A supernatant added to 7 μg/ml as determined by ELISA calibrated with purified rPAPP-A) were incubated with [$^{125}$I]IGFBP-4 in the presence of 5 nM IGF-II. Samples, corresponding to 10,000 cpm per lane, were taken out at selected time points and the reaction stopped by the addition of EDTA to 5 mM. The experiment with sample A was also carried out in the presence of polyclonal anti (PAPP-A/proMBP). A similar time course experiment was performed for comparison of PAPP-A activity in selected column fractions.

Characterization of rPAPP-A. Purified rPAPP-A migrated faster in SDS-PAGE than the disulfide bound 2:2 PAPP-A/ proMBP complex purified from pregnancy serum, and reduced rPAPP-A and PAPP-A from reduced PAPP-A/ proMBP both migrate as a band around 200 kDa. Thus, rPAPP-A is secreted as a dimer of about 400 kDa. A limited degree of degradation that could not be prevented is apparent for both species after reduction of disulfide bonds, and for PAPP-A/proMBP from pregnancy serum without reduction.

Sequence analysis of intact rPAPP-A monomer revealed the expected N-terminal sequence, with the addition of an alanine residue preceeding the N-terminal Glu (Ala-Glu-Ala-Arg-Gly-Ala-Thr-Glu), and the number of N-acetyl-glucosamine (GlcN) monosaccharides per PAPP-A monomer was found through acid hydrolysis to be 22. PAPP-A isolated from PAPP-A/proMBP contains 44 GlcN monomers per PAPP-A polypeptide chain.

The activity of rPAPP-A against IGFBP-4, the only known PAPP-A substrate, was analyzed. As expected, IGFBP-4 was cleaved in the presence, but not in the absence of IGF. The activity of rPAPP-A was inhibited by polyclonal anti(PAPP-A/proMBP), EDTA, and 1,10 phenanthroline, but not by TIMP-1, a broad spectrum inhibitor of matrix metalloproteinases. Supernatants from mock transfected cells, with or without added IGF, did not contain IGFBP-4 proteolytic activity.

An initial experiment revealed that approximately 50 ng of PAPP-A/proMBP complex purified from pregnancy serum was required to obtain the same degree of IGFBP-4 cleavage as 0.1 ng of rPAPP-A. Hypothetically, this difference could be caused by a reduction in the activity of PAPP-A/proMBP during chromatographic processing. Therefore, the IGFBP-4 proteolytic activity of unfractionated pregnancy serum was measured in a time course experiment, and, in a parallel experiment, the activity of pregnancy serum with rPAPP-A added to the same concentration as pregnancy serum PAPP-A. The difference in specific activity between PAPP-A in pregnancy serum and rPAPP-A was estimated from this experiment to be about 100-fold. Incubation of pregnancy serum with polyclonal anti(PAPP-A/proMBP) abolished cleavage of IGFBP-4. Longer incubation (24 h) with twice the amount of pregnancy serum in the presence of inhibitory anti(PAPP-A/proMBP) did not show any IGFBP-4 degradation. As judged from this, PAPP-A is the dominating, perhaps the only proteinase in pregnancy serum, capable of IGFBP-4 cleavage. Thus, PAPP-A that is present in pregnancy serum is strongly inhibited by its binding to proMBP.

Based on the above experiments, it was determined whether pregnancy serum contains traces of uninhibited PAPP-A, not complexed with proMBP. The distribution of PAPP-A antigen in fractions from a Mono Q column loaded with pregnancy serum showed the expected, broad and late eluting PAPP-A/proMBP peak around fraction 43 (FIG. 6A). This peak was preceded by a smaller, less broad peak with a maximum in fraction 24. Interestingly, the elution position and shape of this peak corresponded to that of rPAPP-A when analyzed in the same chromatographic system. Comparison of activity against IGFBP-4 demonstrated that the specific activity of PAPP-A antigen was higher, greater than 25-fold, in the early than in the late eluting peak. Thus, most likely the PAPP-A antigen eluting around fraction 24 is uncomplexed PAPP-A. Because the two PAPP-A peaks are not well separated, the fractions of the early peak also contain a relatively high amount of PAPP-A/proMBP complex. This interpretation was confirmed by Western blotting of the material in the two peaks (FIG. 6B). A parallel Western blot with a proMBP specific monoclonal demonstrated that proMBP was present in the upper, but not in the lower PAPP-A band of the early peak. Uncomplexed, dimeric PAPP-A has not previously been demonstrated in pregnancy serum. To verify that complex formation with proMBP is not a consequence of blood coagulation, separate runs of freshly drawn EDTA treated pregnancy plasma were analyzed on the same system. Again, two PAPP-A peaks were found, and the difference in heights of the early and late eluting peak was the same as for serum. Thus, the vast majority of PAPP-A is present in both pregnancy serum and plasma as PAPP-A/proMBP complex, but a minor fraction (<1%) of PAPP-A is present as an uncomplexed PAPP-A dimer. This uncomplexed fraction has much higher specific activity.

In conclusion, proMBP dramatically inhibits the activity of PAPP-A in pregnancy serum by having formed a covalent complex with PAPP-A. The measurable PAPP-A activity of pregnancy serum stems from a fraction of PAPP-A, less than 1%, which is present as an uninhibited PAPP-A dimer. However, since late eluting PAPP-A is not completely inactive, low amounts of a hypothetical, incompletely inhibited 2:1 PAPP-A/proMBP complex may also be contributing. Such a complex would largely coelute with 2:2 PAPP-A/proMBP complex due to the extreme heterogeneity of the proMBP carbohydrates.

Many proteinases require a propeptide to assist folding and/or secretion. However, because the mature rPAPP-A is antigenic, functional, and secreted abundantly into the culture medium as a dimer of the expected size, a putative PAPP-A propeptide is required neither for folding nor secretion. Often a propeptide functions to retain the proteolytic activity of a zymogen which becomes active in the extracellular compartment only after propeptide cleavage. But the four residue stretch immediately proceeding residue 1 of PAPP-A, Arg-Gln-Gln-Arg, resemble the consensus furin cleavage site. Thus, PAPP-A is likely to be secreted in vivo as an active proteinase. Other regions of the PAPP-A polypeptide, possibly on the C-terminal side of the proteolytic domain, are possibly important for proper folding and secretion as found recently for meprin A, another metzincin metalloproteinase.

Example 5

IGFBP-4 in Follicular Fluid

Follicular fluid was obtained at the time of follicle aspiration for in vitro fertilization (IVF) procedures and from regularly menstruating women as described previously (Chandrasekher, Y. A. et al., *J.Clin. Endocrinol. Metab.*, 1995, 80:2734–2739), centrifuged to remove cellular components, and stored frozen at $-20°$ C. Individual follicles in which the androstenedione to estradiol ratio was $\leq$ to 4 were regarded as estrogen-dominant, and follicles with this ratio >4 were regarded as androgen-dominant. Follicular fluid samples were collected after informed consent was given by subjects, in accordance with the Declaration of Helsinki. The study was approved by the Stanford University Committee on the Use of Human Subjects in Medical Research. Granulosa cells were cultured and serum-free conditioned medium collected as described previously. Cataldo, N. A. et al., *J.Clin. Endocrinol. Metab.*, 1993, 76:207–215. Human IGFBP-4 and IGFBP-5 were provide by Dr. S. Mohan (Loma Linda, Calif.) and Dr. D. L. Andress (Seattle, Wash.), respectively. TIMP-1 was provided by Dr. G. Murphy (Norwich, England).

IGFBP-4 proteolysis was assayed as described in Example 1, by incubating sample at 37° C. for 6 h with [$^{125}$I]IGFBP-4. Reaction products were separated by non-reducing 7.5–15% gradient SDS-PAGE, and visualized by autoradiography.

For some experiments, protease inhibitors (see Table 2) or PAPP-A polyclonal antibody were added to the assay mixture during the 6 h incubation. In others, PAPP-A antibody or nonspecific rabbit IgG was used in conjunction with Protein G-plus/Protein-A-agarose (Oncogene Science) to immunoprecipitate IGFBP-4 protease activity and the sample supernatants were then used in the protease assay.

PAPP-A ELISA A sandwich biotin-tvramide amplified ELISA was performed using a PAPP-A polyclonal antibody for capturing and a collection of PAPP-A monoclonal antibodies for detecting (see Example 4). PAPP-A purified from pregnancy serum was used for calibration.

Incubation of IVF follicular fluid with [$^{125}$I]IGFBP-4 resulted in the loss of intact IGFBP-4 (24-kD nonreducing, 32-kD reducing SDS-PAGE) and the generation of radiolabeled fragments of 18- and 14-kDa. Inclusion of PAPP-A polyclonal antibody in the assay, but not nonspecific rabbit IgG, completely inhibited IGFBP-4 protease activity in follicular fluid. This inhibition was specific for IGFBP-4 proteolysis because PAPP-A antibody did not inhibit [$^{125}$I] IGFBP-5 proteolysis induced by distinct serine proteases in follicular fluid. In other experiments, IGFBP-4 proteolytic activity was effectively immunodepleted from the follicular fluid using specific PAPP-A antibody.

The IGFBP-4 protease activity in IVF follicular fluid was completely suppressed by EDTA and 1,10 phenanthroline, but not by serine protease inhibitors. PMSF, and pefabloc. TIMP-1 had no effect. These experiments, performed twice with similar results, are summarized in Table 2. The results match the inhibitor profile for purified PAPP-A (see above), IGFBP-4 protease activity in human fibroblast conditioned medium (Conover C. A. et al, *J. Clin. Invest.*, 1993, 91:1129–1137) and recombinantly expressed PAPP-A described above.

TABLE 2

Effect of protease inhibitors on IGFBP-4 proteolysis

| Protease Inhibitors | % Inhibition | |
|---|---|---|
| | FF | PAPP-A |
| EDTA, 5 mM | 100 | 100 |
| 1,10 phenantholine, 5 mM | 100 | 100 |
| PMSF, 10 mM | 0 | 20 |
| Pefabloc, 1 mM | 15 | ND |
| TIMP-1, 5 µg/ml | 0 | 0 |

Follicular fluid (FF, 10 µl) or PAPP-A purified from pregnancy serum (500 ng) was incubated with [$^{125}$I]IGFBP-4 and the indicated inhibitors as described above.
ND: not determined.

The data on PAPP-A levels in the different ovarian fluids are presented in Table 3. Using a specific PAPP-A ELISA, $FF_e$ (IVF) follicular fluid contained 1604±315 mIU/L PAPP-A with a range of 260–3728 mIU/L. $FF_e$ (non-IVF) had 160 mIU/L. In comparison, there was no detectable PAPP-A in any of the $FF_a$ samples, in agreement with prior reports of a lack of IGFBP-4 protease activity. Serum-free conditioned medium from luteinized but not non-luteinized granulosa cells in culture also contained PAPP-A immunoreactive material. PAPP-A levels in human fibroblast conditioned medium are included for comparison.

TABLE 3

PAPP-A levels in biological fluids

| Sample | n | PAPP-A (mIU/L) |
|---|---|---|
| Follicular Fluid | | |
| $FF_e$ (IVF) | 12 | 1604 ± 315 |
| $FF_e$ (non-IVF) | 1 | 160 |
| $FF_a$ | 7 | — |
| Conditioned Medium | | |
| luteinized GC | 3 | 106 ± 37 |
| Non-luteinized GC | 2 | — |
| human fibroblast | 4 | 360 ± 40 |

Results are the mean ± SEM of "n" samples.
—: indicates at or below assay sensitivity,
GC: granulosa cell Results are the mean±SEM of "n" samples.—: Indicates at or below assay sensitivity, GC: granulosa cell, $FF_e$: estrogen-dominant follicular fluid, $FF_a$: androgen-dominant follicular fluid.

The IGFBP-4 protease activity in follicular fluid was independent of exogenous IGF. This can be explained by the fact that follicular fluid contains IGF peptides, primarily IGF-II, sufficient to activate IGFBP-4 proteolysis. VanDessel, T. J. H. M., *J. Clin. Endocrinol. Metab.*, 1996, 81:1224–1231. In fact, conditioned medium from luteinized granulosa cells clearly exhibits IGF-dependent IGFBP-4 protease activity in cell-free assay. Cataldo, N. A. et al. *J.Clin. Endocrinol. Metab.*, 1998, 83:179–186; and Chandrasekher, Y. A. et al., *Proceedings of the 28th Annual Meeting of the Society for the Study of Reproduction*, 1995, Davis, Calif. (Abstract 102). Seemingly constitutive IGFBP-4 activity was also reported in human osteoblasts, and shown to be due to endogenous production of IGF.

Without being bound to a particular mechanism, expression of PAPP-A in the ovary at precise stages of follicular development acts to cleave IGFBP-4 allowing increased local bioavailable IGF to stimulate steroidogenesis and promote development of the dominant follicle for ovulation. This is supported by in vitro studies showing that intact IGFBP4 inhibited IGF-stimulated estradiol production in human granulosa cells, whereas proteolyzed IGFBP-4 had no effect. Iwashita M. et al., *Horm. Res.*, 1996. 46(suppl. 1):31–36.

Example 6

Human Coronary Artery Smooth Muscle Cells Express IGFBPs

Primary cultures of adult human coronary artery smooth muscle cells (hCASMC) were obtained from Clonetics (Walkersville, Md.) and cultured in smooth muscle cell basal medium (SmBM, modified MCDB 131) containing 5% fetal bovine serum and antibiotics (50 mg/ml gentamycin, 50 mg/ml amphotericin-B). Cell cultures w ere maintained at 37° C. in a humidified atmosphere of 5% $CO_2$/95% air, and used at passage 5-7 for experiments. These cells stain positive for α-actin smooth muscle expression and negative for factor VII-related antigen.

Cell conditioned hCASMC medium w % as obtained by washing cells twice and changing to serum-free medium (SFM, SmBM+0.1% RIA-grade bovine serum albumin) for a 6-h washout period. Cultures were washed again and changed to fresh SFM with experimental additions. At the end of the incubation, the cell-conditioned medium was centrifuged at 2500 rpm for 30 minutes at 4° C. to remove cellular debris and stored at −80° C.

Cultured hCASMC express specific IGFBPs. Western ligand blotting of 24-h serum-free conditioned medium from three hCASMC cultures indicated predominant IGFBPs of 24 kD, 29–32 kD, and 38/42 kD. Immunoblotting with specific antibodies demonstrated that these forms represented IGFBP-4, IGFBP-5, and IGFBP-3, respectively. Northern analysis of RNA extracted from hCASMC indicated strong expression of IGFBP-3, -4, and -5 mRNA, weak expression of IGFBP-2 and -6 mRNA, and no detectable expression of IGFBP-1 mRNA under basal culture conditions.

Cultured hCASMC also secrete specific IGFBP proteases, hCASMC express PAPP-A mRNA and PAPP-A antigen was detected in the conditioned medium by ELISA (572±38, 740±69, and 1224±515 mIJ/L per 10$^5$ cells at 24 h, 48 h, 72 h, respectively; n=4 per group). The activity of IGFBP-4 protease in hCASMC conditioned medium was inhibited by specific PAPP-A antibodies, hCASMC also secrete serine protease activity specific for IGFBP-5. The identity of this enzyme(s) remains to be determined but its activity was not inhibited by PAPP-A antibody. ProMBP was not detected in hCASMC conditioned medium

Example 7

PAPP-A Binds to the Cell Surface

Flow cytometry was used to assess the binding of PAPP-A to the cell surface of HEK 293 cells either transfected with empty expression vector or with the vector containing cDNA encoding rPAPP-A (see Example 4 for a description of vectors and transfections). Cells 48h post-transfection were detached with 5 mM EDTA, washed in L15 medium containing 2% FBS (L15/FBS) and resuspended to approximately 1,000,000 cells/ml in the same medium. Fifty µl of the cell suspension was incubated with primary antibody (final concentration 5 µg/ml purified PAPP-A specific mAb 234-2) on ice for 30 min. Cells were then washed three times with L15/FBS and incubated with fluorescein isothiocyanate-conjugated goat anti-mouse IgG (heavy and light chain, Zymed Laboratories, San Francisco, Calif.) for 30 min on ice. Cells were fixed in buffer with 1% formaldehyde before flow cytometry on a Becton Dickinson instrument. The results indicated that PAPP-A binds to the surface of HEK 293 cells. Similar results were obtained with other PAPP-A monoclonal antibodies (234-3, 234-4, 234-5, and 234-7).

Example 8

Bioactive Stents Covered by Protease-resistent IGFBP-4 Mutant

This study employs bioactive stents covered by a protease-resistant IGFBP-4 mutant. Since the IGFBP-4 variants are already attached to the stent, they are delivered directly to the desired site of action. Implanting a bioactive stent has the potential to greatly reduce the quantity required to elicit a response compared to systemic delivery. By physically attaching IGFBP-4 variants directly to the metal surface, therapeutic proteins are delivered simultaneously with the implant, precluding the need for additional interventions.

A covalent attachment technique is used to cross-link protease-resistant IGFBP-4 to the surface of stent struts. See, Qin, X. et al., *J. Bone Min. Res.*, 1999, 14:2079–2088 for a description of the protease-resistant IGFBP-4. Approximately 1 mg and 10 mg IGFBP-4 mutant will be tested per stent. The technique for crosslinking IGF system proteins to metal surfaces utilizes organosilanes and bifunctional crosslinkers. This process requires the bonding first of organosilanes to oxides on the metal surface followed by the physical crosslinking of proteins to amino groups on the organosilanes using bifunctional crosslinkers. Various crosslinking techniques have been previously used to attach biological molecules including heparin, cell attachment proteins, and growth factors to various surfaces including metals. The preparation process for crosslinking IGFBP-4 variants to implants consists of acid treating stents with 2.5% hydrofluoric acid-10.5% nitric acid for 1 min and rinsing extensively with ultrapure water. Acid treated stents are siliconized using 3-aminopropyltriethoxysilane (1:50 v/v in 95% ETOH) for 30 min, 23° C. Siliconized stents are rinsed extensively with ultrapure water and placed in a 110° C. oven for 10 min then into a 45° C. oven overnight. IGFBP-4 (1 or 10 mg) is crosslinked to stents using bis-(sulfosuccinimidyl) suberate in PBS, 30 min, 23° C. The crosslinking reaction is terminated using 25 mM Tris, pH 7.5 for 30 min, 23° C. Control stents are acid treated as above and further processing is terminated after the following rinse step. Prepared stents are dried by lyophilization and stored at 4° C. until in vitro or in vivo experiments. Irradiation or cold gas sterilization will be used to sterilize implants.

The bioeffectiveness of the IGFBP-4 bound material is demonstrated in vitro by demonstrating IGF-I binding and inhibition of IGF-1-induced migration of hCASMC after incubation of the material at 37° C. up to 28 days in buffer and in serum-containing medium. Non-cross-linked material is used as a control in these studies.

A direct comparison of the bioactive stent (protease-resistant IGFBP-4 mutant) versus a non-covered (control) stent is performed as follows. Ten outbred juvenile swine are used, 5 in each group. One covered stent is placed in an angiographically suitable (appropriate diameter, no major side-branch) coronary artery and one non-covered control stent of similar size will be placed in another appropriately sized coronary artery. Based on previous experience, 10 treated arteries and 10 control arteries are sufficient to detect significant differences in neointimal formation and lumen reduction.

The primary response variable is the extent of neointimal formation in the two conditions at 28 days, the necessary time for restenosis to occur in the porcine model. Twenty-eight days (±2 days) post-procedure, the animal is euthanized after performing a quantitative angiographic evaluation of the treated coronary arteries. The heart is then perfusion fixed and the stented segments processed, sectioned, and stained following standard Histology lab protocols. H & E stain and elastic van Gieson stains are performed on serial sections through the length of the stent.

Quantitative angiography is important to measure vessel diameter pre- and post-stent placement and at the 28-day follow-up. The quantitative coronary angiography (QCA) measurements that are performed include: minimum lumen diameter; distal and proximal reference lumen diameter; % stenosis [minimum lumen diameter/reference lumen diameter (proximal and distal)×100].

Histologic measurements provide an understanding of the differential effect of both stents (covered and control). These will be made from proximal, middle, and distal portions of the covered stent and control stent. The cross-sectional measurements include: lumen area, internal elastic lamina (IEL) and/or stent area, neointimal area, medial area, external elastic lamina (EEL) area, adventitial area, radial intimal thickness at each strut wire (neointimal thickness), percent in-stent stenosis, injury score at each strut wire. A vessel injury score is calculated using the method described by Schwartz et al., supra, as follows: 0, intact mean endothelium; 1 endothelial denudation; 2, IEL laceration; 3, IEL and media laceration; and 4, EEL laceration. Neointimal thickness is measured at each wire site. The reference vessel luminal area is obtained from proximal and distal sites that were not stented.

A sample size of 10 animals per group is chosen so that the projected difference in neointimal thickness of 0.1 mm at a power of 0.8 can be detected. Statistical analysis is performed at injury and neointima at each wire site. Regression modeling is used to account for injury and the injury-dependent neointimal response. Three models are used to establish whether there are differences in intercepts, slopes, or both intercepts and slopes across the two groups studied. The statistical significance of these variables determines the significance of the group to either slope or intercept of neointima and injury. Differences between treatment groups at each injury level are analyzed by the Tukey-Kramer multiple comparisons t test.

The in vitro experiments will demonstrate that the cross-linked IGFBP-4 mutant is functional over time under physiological conditions. These experiments will validate resistance of the IGFBP-4 mutant to general proteolysis by serum proteases. The endpoint will be significant inhibition of hCASMC migration by the crossed-linked IGFBP-4 mutant after 7 days of incubation. Endpoints for the in vivo studies will be measured as angiographic (in-stent stenosis) and histological (intimal thickening) reduction observed in the covered stents versus the non-covered stents. In addition, data from the experimental stents will be compared to historical covered stent data.

Example 9

Human Coronary Atherosclerotic Plaques Express IGFBP-4 Protease

Fourteen plaques, comprising four stable plaques, five ruptured plaques and five plaque erosions, obtained from necropsy material of sudden cardiac death patients were examined. Immunohistochemical staining was performed for PAPP-A, IGF-1, and IGFBP-4. The cellular composition of the plaque was determined using antibodies for α-smooth muscle actin and macrophages. PAPP-A expression was substantially higher in the β-actin cells from the coronary media, the plaque, and the media of the vasa vasorum. Endothelium and adventitia showed significantly lower levels of PAPP-A ($p<0.05$). No PAPP-A was detected in macrophages, and no differences were observed between stable and unstable plaques. There was no detectable IGF-I expression, and IGFBP-4 staining was diffuse in all cell types.

Thus, PAPP-A is present in human atherosclerotic plaques. PAPP-A increases local IGF-I bioavailability, and may be a marker for atherosclerosis progression as well as a therapeutic target to limit plaque growth.

OTHER EMBODIMENTS

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting PAPP-A- in a biological sample comprising contacting said biological sample with an antibody having specific binding affinity for PAPP-A-, but not PAPP-A-/pro major basic protein complex, to detect PAPP-A- in said biological sample.

* * * * *

SEQUENCE LISTING

```
<160> NUMBER OF SEQ ID NOS: 30

<210> SEQ ID NO 1
<211> LENGTH: 7
<212> TYPE: PRT
<213> ORGANISM: Homo sapiens

<400> SEQUENCE: 1

Ala Asp Leu Glu Leu Pro Arg
 1               5

<210> SEQ ID NO 2
<211> LENGTH: 11
<212> TYPE: PRT
<213> ORGANISM: Homo sapiens

<400> SEQUENCE: 2

Ser Pro Ala Val Ile Thr Gly Leu Tyr Asp Lys
 1               5                   10

<210> SEQ ID NO 3
<211> LENGTH: 20
<212> TYPE: PRT
<213> ORGANISM: Homo sapiens

<400> SEQUENCE: 3

Ser Tyr Leu Pro Gly Gln Trp Val Tyr Leu Ala Ala Thr Tyr Asp Gly
 1               5                   10                  15

Gln Phe Met Lys
            20

<210> SEQ ID NO 4
<211> LENGTH: 15
<212> TYPE: PRT
<213> ORGANISM: Homo sapiens

<400> SEQUENCE: 4

Glu Gln Val Asp Phe Gln His His Gln Leu Ala Glu Ala Phe Lys
 1               5                   10                  15
```

```
<210> SEQ ID NO 5
<211> LENGTH: 16
<212> TYPE: PRT
<213> ORGANISM: Homo sapiens

<400> SEQUENCE: 5

Thr Ile Ser Tyr Pro Tyr Ser Leu Ala Gln Thr Thr Phe Trp Leu Arg
 1               5                  10                  15

<210> SEQ ID NO 6
<211> LENGTH: 16
<212> TYPE: PRT
<213> ORGANISM: Homo sapiens

<400> SEQUENCE: 6

Ser Phe Asp Asn Phe Asp Pro Val Thr Leu Ser Ser Cys Gln Arg Gly
 1               5                  10                  15

<210> SEQ ID NO 7
<211> LENGTH: 11
<212> TYPE: PRT
<213> ORGANISM: Artificial Sequence
<220> FEATURE:
<223> OTHER INFORMATION: consensus binding motif
<221> NAME/KEY: VARIANT
<222> LOCATION: (1)...(11)
<223> OTHER INFORMATION: Xaa = Any Amino Acid

<400> SEQUENCE: 7

His Glu Xaa Xaa His Xaa Xaa Gly Xaa Xaa His
 1               5                  10

<210> SEQ ID NO 8
<211> LENGTH: 23
<212> TYPE: DNA
<213> ORGANISM: Homo sapiens

<400> SEQUENCE: 8
aaacccattt tattgcaggg agg                                           23

<210> SEQ ID NO 9
<211> LENGTH: 22
<212> TYPE: DNA
<213> ORGANISM: Homo sapiens

<400> SEQUENCE: 9
ctgtggttgt gtgacaaatg gc                                            22

<210> SEQ ID NO 10
<211> LENGTH: 33
<212> TYPE: DNA
<213> ORGANISM: Homo sapiens

<400> SEQUENCE: 10
cagtcagctg ctcaacggaa ggactcacat tgg                                33

<210> SEQ ID NO 11
<211> LENGTH: 19
<212> TYPE: DNA
<213> ORGANISM: Homo sapiens

<400> SEQUENCE: 11
ggaggctctg ggactgcac                                                19
```

```
<210> SEQ ID NO 12
<211> LENGTH: 41
<212> TYPE: DNA
<213> ORGANISM: Homo sapiens

<400> SEQUENCE: 12
aacgggaagc tcactggcat gatgacatca agaaggtggt g                41

<210> SEQ ID NO 13
<211> LENGTH: 21
<212> TYPE: DNA
<213> ORGANISM: Homo sapiens

<400> SEQUENCE: 13
ccaccaccct gatgctgtag c                                      21

<210> SEQ ID NO 14
<211> LENGTH: 23
<212> TYPE: DNA
<213> ORGANISM: Homo sapiens

<400> SEQUENCE: 14
cacccagcac aatgaagatc aag                                    23

<210> SEQ ID NO 15
<211> LENGTH: 23
<212> TYPE: DNA
<213> ORGANISM: Homo sapiens

<400> SEQUENCE: 15
gtcaagaaag ggtgtaacgc aac                                    23

<210> SEQ ID NO 16
<211> LENGTH: 20
<212> TYPE: DNA
<213> ORGANISM: Homo sapiens

<400> SEQUENCE: 16
cagtcagctg ctcaacggaa                                        20

<210> SEQ ID NO 17
<211> LENGTH: 19
<212> TYPE: DNA
<213> ORGANISM: Homo sapiens

<400> SEQUENCE: 17
ggaggctctg ggactgcac                                         19

<210> SEQ ID NO 18
<211> LENGTH: 23
<212> TYPE: DNA
<213> ORGANISM: Homo sapiens

<400> SEQUENCE: 18
ttagtcaagc ttggtttact tgc                                    23

<210> SEQ ID NO 19
<211> LENGTH: 21
<212> TYPE: DNA
<213> ORGANISM: Homo sapiens

<400> SEQUENCE: 19
ggaagtcttc tgaggcagtg g                                      21
```

<210> SEQ ID NO 20
<211> LENGTH: 21
<212> TYPE: DNA
<213> ORGANISM: Homo sapiens

<400> SEQUENCE: 20
aacgggaagc tcactggcat g                                        21

<210> SEQ ID NO 21
<211> LENGTH: 21
<212> TYPE: DNA
<213> ORGANISM: Homo sapiens

<400> SEQUENCE: 21
ccaccaccct gttgctgtag c                                        21

<210> SEQ ID NO 22
<211> LENGTH: 28
<212> TYPE: PRT
<213> ORGANISM: Artificial Sequence
<220> FEATURE:
<223> OTHER INFORMATION: artificial signal peptide

<400> SEQUENCE: 22

Met Lys Asp Ser Cys Ile Thr Val Met Ala Met Ala Leu Leu Ser Gly
 1               5                  10                  15

Phe Phe Phe Phe Ala Pro Ala Ser Ser Tyr Ala Ala
            20                  25

<210> SEQ ID NO 23
<211> LENGTH: 30
<212> TYPE: DNA
<213> ORGANISM: Homo sapiens

<400> SEQUENCE: 23
cctgcatcac tgtgatggcc atggcgctgc                               30

<210> SEQ ID NO 24
<211> LENGTH: 31
<212> TYPE: DNA
<213> ORGANISM: Homo sapiens

<400> SEQUENCE: 24
tgtctgggtt cttttcttc gcgccggcct c                              31

<210> SEQ ID NO 25
<211> LENGTH: 30
<212> TYPE: DNA
<213> ORGANISM: Homo sapiens

<400> SEQUENCE: 25
gagctatgcc gcggaagcta ggggcgccat                               30

<210> SEQ ID NO 26
<211> LENGTH: 30
<212> TYPE: DNA
<213> ORGANISM: Homo sapiens

<400> SEQUENCE: 26
gcggcatagc tcgaggccgg cgcgaagaaa                               30

<210> SEQ ID NO 27

-continued

```
<211> LENGTH: 30
<212> TYPE: DNA
<213> ORGANISM: Homo sapiens

<400> SEQUENCE: 27
aagaacccag acagcagcgc catggccatc                              30

<210> SEQ ID NO 28
<211> LENGTH: 30
<212> TYPE: DNA
<213> ORGANISM: Homo sapiens

<400> SEQUENCE: 28
acagtgatgc aggaatcctt cataagctta                              30

<210> SEQ ID NO 29
<211> LENGTH: 18
<212> TYPE: DNA
<213> ORGANISM: Homo sapiens

<400> SEQUENCE: 29
ctaagcttat gaaggatt                                           18

<210> SEQ ID NO 30
<211> LENGTH: 18
<212> TYPE: DNA
<213> ORGANISM: Homo sapiens

<400> SEQUENCE: 30
atggcgcccc tagcttcc                                           18
```